(12) United States Patent
Matsuyama et al.

(10) Patent No.: US 9,428,733 B2
(45) Date of Patent: Aug. 30, 2016

(54) METHOD FOR OBTAINING PANCREATIC ENDOCRINE CELLS FROM ADIPOSE TISSUE-ORIGIN CELLS

(75) Inventors: Akifumi Matsuyama, Suita (JP); Hiroshi Komoda, Suita (JP); Yoshiki Sawa, Suita (JP); Yuzuru Kanakura, Suita (JP)

(73) Assignee: AKIFUMI MATSUYAMA, Osaka-shi, Osaka (JP)

( * ) Notice: Subject to any disclaimer, the term of this patent is extended or adjusted under 35 U.S.C. 154(b) by 571 days.

(21) Appl. No.: 13/507,249

(22) Filed: Jun. 15, 2012

(65) Prior Publication Data

US 2013/0109092 A1 May 2, 2013

Related U.S. Application Data

(62) Division of application No. 12/083,018, filed as application No. PCT/JP2006/316007 on Aug. 14, 2006, now abandoned.

(30) Foreign Application Priority Data

Oct. 5, 2005 (JP) ................................ 2005-292613

(51) Int. Cl.
*C12N 5/0775* (2010.01)
*A61K 35/12* (2015.01)
*C12N 5/071* (2010.01)
*G01N 33/50* (2006.01)

(52) U.S. Cl.
CPC ........... *C12N 5/0667* (2013.01); *C12N 5/0676* (2013.01); *C12N 5/0678* (2013.01); *G01N 33/507* (2013.01); *A61K 35/12* (2013.01); *C12N 2500/25* (2013.01); *C12N 2500/32* (2013.01); *C12N 2500/38* (2013.01); *C12N 2501/115* (2013.01); *C12N 2501/335* (2013.01); *C12N 2503/02* (2013.01); *C12N 2506/1384* (2013.01); *C12N 2533/52* (2013.01)

(58) Field of Classification Search
CPC .. A61K 35/35; C12N 5/0667; C12N 5/0678; C12N 5/0676; C12N 2506/1384
USPC ................................. 435/325, 378
See application file for complete search history.

(56) References Cited

U.S. PATENT DOCUMENTS

| 2003/0124721 | A1 | 7/2003 | Cheatham et al. | |
|---|---|---|---|---|
| 2006/0045872 | A1* | 3/2006 | Miguel et al. | 424/93.7 |
| 2006/0182724 | A1 | 8/2006 | Riordan | |
| 2009/0304643 | A1 | 12/2009 | Khurgel et al. | |

FOREIGN PATENT DOCUMENTS

| WO | WO 97/015310 | | 5/1997 | |
|---|---|---|---|---|
| WO | WO 01/039784 | A1 | 6/2001 | |
| WO | WO 02/079457 | A1 | 10/2002 | |
| WO | WO 03/022988 | A2 | 3/2003 | |
| WO | WO 03/039489 | A2 | 5/2003 | |
| WO | WO 03/050249 | A2 | 6/2003 | |
| WO | WO 03085099 | A2 * | 10/2003 | ........... C12N 5/0667 |

OTHER PUBLICATIONS

Gronthos et al. Surface Protein Characterization of Human Adipose Tissue-Derived Stromal Cells. Journal of Cellular Physiology 189:54±63 (2001).*
Pereboeva et al. Approaches to Utilize Mesenchymal Progenitor Cells as Cellular Vehicles. Stem Cells. 2003;21:389-404.*
Lonza: Trypsin/ Trypsin-Versene (EDTA)/ Versene (EDTA). 2009. p. 1.*
U.S. Appl. No. 12/083,018, Final Office Action mailed Jun. 4, 2014 (8 pages).
U.S. Office Action (U.S. Appl. No. 12/083,018) dated Nov. 4, 2013.
Japanese Office Action (Application No. 2011-096351) dated Jul. 2, 2013.
Japanese Office Action (Japanese Patent Application No. 2011-096351); dated: Jan. 29, 2013; with English Translation; pp. 1-4.
Andrea Quaroni et al., "Epitheloid Cell Cultures From Rat Small Intestine", J. Cell Biology, The Rockefeller University Press; vol. 80(2), Feb. 1979; pp. 248-265.
Tung-Tien Sun et al. "Cell Culture of Mammalian Thymic Epithelial Cells: Growth, Structural, and Antigenic Properties"; Cellular Immunology 83(1); (1984); pp. 1-13.
Manas K. Majumdar et al. "Characterization and Functionality of Cell Surface Molecules on Human Mesenchymal Stem Cells", J. Biomed. Sci. 2003; 10(2); (2003) pp. 228-241.
Vaerman et al., Evaluation of real-time PCR data, Journal of Biological Regulators and Homeostatic Agents, 2004; 18: 212-4.
Barber et al., GAPDH as a housekeeping gene: analysis of GAPDH mRNA expression in a panel of 72 human tissues, Physiol Genomics 21: 389-395, 2005.
Office Action—Japanese Patent Application No. 2007-538655 mailed Aug. 9, 2011.
E. Messina et al., "Isolation and Expansion of Adult Cardiac Stem Cells From Human and Murine Heart", *Circulation Research*, vol. 95, No. 9, pp. 911-921, 2004.

(Continued)

*Primary Examiner* — Taeyoon Kim
(74) *Attorney, Agent, or Firm* — Nixon Peabody LLP; Jeffrey L. Costellia

(57) ABSTRACT

A method of obtaining pancreatic endocrine cells from cells originating in an adipose tissue characterized by comprising culturing the adipose tissue-origin cells; the pancreatic endocrine cells that can be obtained thereby; a method of treating or preventing a disease caused by the hypofunction in pancreatic endocrine cells wherein the above-described pancreatic endocrine cells are used; a method of screening a substance capable of promoting or inhibiting the differentiation into pancreatic endocrine cells characterized by comprising adding a candidate substance to a medium in the course of culturing adipose tissue-origin cells to obtain the pancreatic endocrine cells; and so on.

1 Claim, 22 Drawing Sheets

(12 of 22 Drawing Sheet(s) Filed in Color)

(56) References Cited

OTHER PUBLICATIONS

P.W. Dyce et al., "Stem cells with multilineage potential derived from porcine skin", *Biochemical and Biophysics Research Communications*, vol. 316, No. 3, pp. 651-658, 2004.

Kang et al., Expression of Telomerase Extends the Lifespan and Enhances Osteogenic Differentiation of Adipose Tissue-Derived Stromal Cells, Stem Cells 2004;22:1356-1372.

Office Action—Japanese Patent Application No. 2007-538655 mailed Feb. 22, 2011.

T. Kodera et al., "Tonyobyo to Saisei Iryo, I Sui β Saibo Saisei Iryo no Kinmirai, Sui β Saibo saisei Kiko—Overview-", Diabetes Frontier, vol. 17, No. 3, pp. 308-313 (Jun. 2006) and English translation thereof.

J. Shapiro et al., "Islet Transplantation in Seven Patients With Type 1 Diabetes Mellitus Using a Glucocorticoid-Free Immunosuppressive Regimen", *The New England Journal of Medicine*, vol. 343, No. 4, pp. 230-238, Jul. 27, 2000.

E.A. Ryan et al., "Five-Year Follow-Up After Clinical Islet Transplantation", *Diabetes*, vol. 54, No. 7, Health & Medical Complete, pp. 2060-2069, Jul. 2005.

S. Matsumoto et al., "Insulin Independence After Living-Donor Distal Pancreatectomy and Islet Allotransplantation", www.thelancet.com, vol. 365, pp. 1642-1644, May 7, 2005.

H. Segev et al., "Differentiation of Human Embryonic Stem Cells into Insulin-Producing Clusters", *Stem Cells*, Rapid Communication, vol. 22, pp. 265-274, (2004).

J. Rajagopal et al., "Insulin Staining of ES Cell Progeny from Insulin Uptake", *Science* AAAS, vol. 299, p. 363, Jan. 17, 2003.

S. Bonner-Weir et al., "New Sources of Pancreatic β-Cells", Nature Biotechnology, vol. 23, No. 7, pp. 857-861, Jul. 2005.

S.U. Devaskar et al., "Insulin Gene Expression and Insulin Synthesis in Mammalian Neuronal Cells", *The Journal of Biological Chemistry*, vol. 269, No. 11, pp. 8445-8454 (1994).

\* cited by examiner

```
                        SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: PCR forward primer to amplify insulin mRNA

<400> SEQUENCE: 1
agcctttgtg aaccaacacc                                              20

<210> SEQ ID NO 2
<211> LENGTH: 20
<212> TYPE: DNA
<213> ORGANISM: Artificial Sequence
<220> FEATURE:
<223> OTHER INFORMATION: PCR reverse primer to amplify insulin mRNA

<400> SEQUENCE: 2
gctggtagag ggagcagatg                                              20

<210> SEQ ID NO 3
<211> LENGTH: 19
<212> TYPE: DNA
<213> ORGANISM: Artificial Sequence
<220> FEATURE:
<223> OTHER INFORMATION: PCR forward primer to amplify Glucagon mRNA

<400> SEQUENCE: 3
aggcagaccc actcagtga                                               19

<210> SEQ ID NO 4
<211> LENGTH: 20
<212> TYPE: DNA
<213> ORGANISM: Artificial Sequence
<220> FEATURE:
<223> OTHER INFORMATION: PCR reverse primer to amplify Glucagon mRNA

<400> SEQUENCE: 4
aacaatggcg acctcttctg                                              20

<210> SEQ ID NO 5
<211> LENGTH: 18
```

```
<212> TYPE: DNA
<213> ORGANISM: Artificial Sequence
<220> FEATURE:
<223> OTHER INFORMATION: PCR forward primer to amplify Somtatostatin
      mRNA

<400> SEQUENCE: 5
tgcgctgtcc atcgtcct                                                 18

<210> SEQ ID NO 6
<211> LENGTH: 20
<212> TYPE: DNA
<213> ORGANISM: Artificial Sequence
<220> FEATURE:
<223> OTHER INFORMATION: PCR reverse primer to amplify Somatostatin
      mRNA

<400> SEQUENCE: 6
gccatagccg ggtttgagtt                                               20

<210> SEQ ID NO 7
<211> LENGTH: 24
<212> TYPE: DNA
<213> ORGANISM: Artificial Sequence
<220> FEATURE:
<223> OTHER INFORMATION: PCR forward primer to amplify IAPP mRNA

<400> SEQUENCE: 7
gagagagcca ctgaattact tgcc                                          24

<210> SEQ ID NO 8
<211> LENGTH: 22
<212> TYPE: DNA
<213> ORGANISM: Artificial Sequence
<220> FEATURE:
<223> OTHER INFORMATION: PCR reverse primer to amplify IAPP mRNA

<400> SEQUENCE: 8
cctgacctta tcgtgatctg cc                                            22

<210> SEQ ID NO 9
<211> LENGTH: 25
<212> TYPE: DNA
<213> ORGANISM: Artificial Sequence
<220> FEATURE:
<223> OTHER INFORMATION: PCR forward primer to amplify Pdx-1 mRNA

<400> SEQUENCE: 9
ggatgaagtc taccaaagct cacgc                                         25

<210> SEQ ID NO 10
<211> LENGTH: 25
<212> TYPE: DNA
<213> ORGANISM: Artificial Sequence
<220> FEATURE:
<223> OTHER INFORMATION: PCR reverse primer to ampify Pdx-1 mRNA

<400> SEQUENCE: 10
ccagatcttg atgtgtctct cggtc                                         25

<210> SEQ ID NO 11
<211> LENGTH: 22
<212> TYPE: DNA
<213> ORGANISM: Artificial Sequence
<220> FEATURE:
<223> OTHER INFORMATION: PCR forward primer to amplify Islet-1 mRNA
```

<400> SEQUENCE: 11 gatttccta tgtgttggtt gc                                            22

<210> SEQ ID NO 12
<211> LENGTH: 22
<212> TYPE: DNA
<213> ORGANISM: Artificial Sequence
<220> FEATURE:
<223> OTHER INFORMATION: PCR reverse primer to amplify Islet-1 mRNA

<400> SEQUENCE: 12
cttccactgg gttagcctgt aa                                           22

<210> SEQ ID NO 13
<211> LENGTH: 22
<212> TYPE: DNA
<213> ORGANISM: Artificial Sequence
<220> FEATURE:
<223> OTHER INFORMATION: PCR forward primer to amplify Nkx6.1 mRNA

<400> SEQUENCE: 13
gttcctcctc ctcctcttcc tc                                           22

<210> SEQ ID NO 14
<211> LENGTH: 22
<212> TYPE: DNA
<213> ORGANISM: Artificial Sequence
<220> FEATURE:
<223> OTHER INFORMATION: PCR reverse primer to amplify Nkx6.1 mRNA

<400> SEQUENCE: 14
aagatctgct gtccggaaaa ag                                           22

<210> SEQ ID NO 15
<211> LENGTH: 27
<212> TYPE: DNA
<213> ORGANISM: Artificial Sequence
<220> FEATURE:
<223> OTHER INFORMATION: PCR forward primer to amplify PC1/3 mRNA

<400> SEQUENCE: 15
ttggctgaaa gagaacggga tacatct                                      27

<210> SEQ ID NO 16
<211> LENGTH: 27
<212> TYPE: DNA
<213> ORGANISM: Artificial Sequence
<220> FEATURE:
<223> OTHER INFORMATION: PCR reverse primer to amplify PC1/3 mRNA

<400> SEQUENCE: 16
acttctttgg tgattgcttt ggcggtg                                      27

<210> SEQ ID NO 17
<211> LENGTH: 24
<212> TYPE: DNA
<213> ORGANISM: Artificial Sequence
<220> FEATURE:
<223> OTHER INFORMATION: PCR forward primer to amplify PC2 mRNA

<400> SEQUENCE: 17
gcatcaagca cagacctaca ctcg                                         24

<210> SEQ ID NO 18
<211> LENGTH: 25

```
<212> TYPE: DNA
<213> ORGANISM: Artificial Sequence
<220> FEATURE:
<223> OTHER INFORMATION: PCR reverse primer to amplify PC2 mRNA

<400> SEQUENCE: 18
gagacacaac cacccttcat ccttc                                       25

<210> SEQ ID NO 19
<211> LENGTH: 20
<212> TYPE: DNA
<213> ORGANISM: Artificial Sequence
<220> FEATURE:
<223> OTHER INFORMATION: PCR forward primer to amplify GAPDH mRNA

<400> SEQUENCE: 19
gtcagtggtg gacctgacct                                             20

<210> SEQ ID NO 20
<211> LENGTH: 20
<212> TYPE: DNA
<213> ORGANISM: Artificial Sequence
<220> FEATURE:
<223> OTHER INFORMATION: PCR reverse primer to amplify GAPDH mRNA

<400> SEQUENCE: 20
aggggagatt cagtgtggtg                                             20
```

METHOD FOR OBTAINING PANCREATIC ENDOCRINE CELLS FROM ADIPOSE TISSUE-ORIGIN CELLS

SEQUENCE LISTING

The instant application contains a Sequence Listing which has been submitted in ASCII format via EFS-Web and is hereby incorporated by reference in its entirety. Said ASCII copy was created on Jan. 7, 2013, is named Sequence Listing 740630-188.txt and is 4,499 bytes in size.

TECHNICAL FIELD

The present invention relates to a method for obtaining pancreatic endocrine cells from adipose tissue-derived cells, pancreatic endocrine cells which are obtainable by the method, a method for treatment or prevention of diseases caused by decreases in the function of pancreatic endocrine cells using the pancreatic endocrine cells, a method for screening a substance which promotes or suppresses differentiation to pancreatic endocrine cells, a kit for the method and the like.

BACKGROUND ART

Diabetes is a disease group which causes hyperglycemia due to absolute or relative lack of an insulin action. Because the persistence of hyperglycemia induces neuropathy, retinopathy, nephropathy, and atherosclerotic disease, prevention or treatment of diabetes is one of the important targets in the present medicine. Diabetes is divided into type 1 diabetes and type 2 diabetes depending on the pathogenic mechanism. Type 1 diabetes is a disease in which pancreatic β cells are destroyed by autoimmunity and disappeared, and is characterized in that the absolute lack of an insulin action. Thus, an insulin treatment is generally used. There are some types of diabetes such as Brittle type, in which control of insulin is difficult. Type 2 diabetes is characterized in that relative lack of an insulin action, and is caused by the complication of so-called metabolic syndrome. Thus, the main therapy is administering drugs for improvement of insulin resistance preventing an insulin action, or drugs for acceleration of insulin secretion from pancreatic β cells. The patients with type 2 diabetes in Europe and the United States have the insulin resistance as its main pathology, while the patients with type 2 diabetes in Japan additionally have exhaustion, depletion, and disappearance of pancreatic β cells. Therefore, in Japan, the therapy which replaces insulin is essential for both type 1 diabetes and type 2 diabetes.

Recently, transplantation of pancreatic islets are conducted. In some cases, withdrawal from insulin is observed, and in other cases in which withdrawal from insulin is not achieved, improvement in control of insulin is observed (Non-Patent Documents 1, 2 and 3). However, because a donor, which may be living or dead, is required for transplantation of pancreatic islets, its resource is restricted. In order to solve such problem, attempts to generate pancreatic islets have been made. Recently, it was reported that generation of pancreatic islets from ES cells was successful (Non-Patent Document 4). However, transplanting the insulin-secreting cells from these cells has not only the problem of HLA incompatibility but also the ethical problems, and has the possibility of existing a virus or antigen from an animal of a different species. Additionally, there is a limit to types and amounts of the established ES cells. Therefore, it is difficult to provide the insulin-secreting cells to all patients who require transplanting thereof.

If the insulin-secreting cell is the cell which can be obtained from autologous somatic stem cells, it is considered that there is no need to consider the problem of HLA incompatibility, and there are medical and social advantages rather than the ethical problems. However, it has not been reported that the generation of the pancreatic islets from somatic stem cells is successful.

Non-Patent Document 1: Shapiro A M et al., N Engl J Med. 2000 Jul. 27; 343(4): 289-90

Non-Patent Document 2: Ryan EA et al., Diabetes. 2005 July; 54(7): 2060-9

Non-Patent Document 3: Matsumoto S et al., Lancet. 2005 May 7-13; 365(9471): 1603-1604

Non-Patent Document 4: Segev H et al., Stem Cells 2004; 22: 265-274

DISCLOSURE OF THE INVENTION

Problems to be Solved by the Invention

The problem to be solved by the present invention is to provide a method for treatment of diabetes without the problems as described above. Specifically, the problem of the present invention is to provide a method for obtaining pancreatic endocrine cells from adipose tissue-derived cells, pancreatic endocrine cells which are obtainable by the method, a method for screening a substance which promotes or suppresses differentiation to pancreatic endocrine cells, a kit for the method and the like.

Means to Solve the Problems

As a result of intensive studies in view of the situation as described above, the present inventors have found that, by obtaining undifferentiated cells from adipose tissue-derived cells, and differentiating the undifferentiated cells to pancreatic precursor cells, pancreatic endocrine precursor cells, and prepancreatic endocrine cells, finally pancreatic endocrine cells can be obtained. Thus the present invention has been completed.

Accordingly, the present invention provides:

(1) a method for obtaining pancreatic endocrine cells from adipose tissue-derived cells, which comprises culturing the adipose tissue-derived cells;

(2) the method according to (1), which comprises the step of obtaining undifferentiated cells from the adipose tissue-derived cells;

(3) the method according to (2), which further comprises the step of differentiating prepancreatic endocrine cells to pancreatic endocrine cells;

(4) the method according to (3), which comprises the following steps (a) to (e):
   (a) obtaining the undifferentiated cells from the adipose tissue-derived cells,
   (b) differentiating the undifferentiated cells to pancreatic precursor cells,
   (c) differentiating the pancreatic precursor cells to pancreatic endocrine precursor cells,
   (d) differentiating the pancreatic endocrine precursor cells to the prepancreatic endocrine cells, and
   (e) differentiating the prepancreatic endocrine cells to the pancreatic endocrine cells;

(5) the method according to any one of (2) to (4), wherein the step of obtaining the undifferentiated cells from the adipose tissue-derived cells is the step of culturing the adipose tissue-derived cells in suspended state to form adipospheres;

(6) the method according to any one of (1) to (5), wherein the pancreatic endocrine cells are insulin-secreting cells;

(7) the method according to any one of (1) to (6), wherein the pancreatic endocrine cells form a pancreatic islet;

(8) a pancreatic endocrine cell, which is obtainable by the method according to any one of (1) to (7);

(9) the cell according to (8), which is an insulin-secreting cell;

(10) the cell according to (8) or (9), which forms a pancreatic islet;

(11) a method for treatment or prevention of diseases caused by decrease in the function of pancreatic endocrine cells, which comprises administering the pancreatic endocrine cells obtainable by the method according to any one of (1) to (7) to a subject;

(12) the method according to (11), wherein the pancreatic endocrine cells are insulin-secreting cells;

(13) the method according to (11) or (12), wherein the pancreatic endocrine cells form a pancreatic islet;

(14) the method according to any one of (11) to (13), wherein the disease is diabetes;

(15) a method for screening a substance which promotes differentiation to pancreatic endocrine cells, which comprises, when culturing adipose tissue-derived cells to obtain the pancreatic endocrine cells, adding a candidate substance to a culture medium, wherein promoted differentiation to the pancreatic endocrine cells compared with differentiation in a medium without the candidate substance indicates that the candidate substance is a substance which promotes differentiation to pancreatic endocrine cells;

(16) the method according to (15), wherein the pancreatic endocrine cells are insulin-secreting cells;

(17) the method according to (15) or (16), wherein the pancreatic endocrine cells form a pancreatic islet;

(18) a substance which promotes differentiation to pancreatic endocrine cells, which is obtainable by the method according to any one of (15) to (17);

(19) a method for screening a substance which suppresses differentiation to pancreatic endocrine cells, which comprises, when culturing adipose tissue-derived cells to obtain the pancreatic endocrine cells, adding a candidate substance to a culture medium, wherein suppressed differentiation to the pancreatic endocrine cells compared with differentiation in a medium without the candidate substance indicates that the candidate substance is a substance which suppresses differentiation to pancreatic endocrine cells;

(20) the method according to (19), wherein the pancreatic endocrine cells are insulin-secreting cells;

(21) the method according to (19) or (20), wherein the pancreatic endocrine cells form a pancreatic islet;

(22) a substance which suppresses differentiation to pancreatic endocrine cells, which is obtainable by the method according to any one of (19) to (21);

(23) a kit for screening a substance which promotes or suppresses differentiation to pancreatic endocrine cells, which is used in the method according to any one of (15) to (17) or (19) to (21);

(24) a method for screening a substance which increases activity of pancreatic endocrine cells, which comprises, culturing the pancreatic endocrine cells obtained by culturing adipose tissue-derived cells in a culture medium with a candidate substance, wherein difference of the amount of a substance secreted from the pancreatic endocrine cells compared with the amount in a medium without the candidate substance indicates that the candidate substance is a substance which increases activity of pancreatic endocrine cells;

(25) the method according to (24), wherein the substance secreted from the pancreatic endocrine cells is insulin, C-peptide, glucagon, somatostatin, or pancreatic peptide;

(26) the method according to (24) or (25), wherein the pancreatic endocrine cells are insulin-secreting cells;

(27) the method according to any one of (24) to (26), wherein the pancreatic endocrine cells form a pancreatic islet;

(28) a substance which increases activity of pancreatic endocrine cells, which is obtainable by the method according to any one of (24) to (27);

(29) a method for screening a substance which decreases activity of pancreatic endocrine cells, which comprises, culturing the pancreatic endocrine cells obtained by culturing adipose tissue-derived cells in a culture medium with a candidate substance, wherein difference of the amount of a substance secreted from the pancreatic endocrine cells compared with the amount in a medium without the candidate substance indicates that the candidate substance is a substance which decreases activity of pancreatic endocrine cells;

(30) the method according to (29), wherein the substance secreted from the pancreatic endocrine cells is insulin, C-peptide, glucagon, somatostatin, or pancreatic peptide;

(31) the method according to (29) or (30), wherein the pancreatic endocrine cells are insulin-secreting cells;

(32) the method according to any one of (29) to (31), wherein the pancreatic endocrine cells form a pancreatic islet;

(33) a substance which decreases activity of pancreatic endocrine cells, which is obtainable by the method according to any one of (29) to (32);

(34) a kit for screening a substance which increases or decreases activity of pancreatic endocrine cells, which is used in the method according to any one of (24) to (27) or (29) to (32);

(35) a method for obtaining a pancreatic islet from adipose tissue-derived cells, which comprises culturing the adipose tissue-derived cells;

(36) the method according to (35), which comprises the step of obtaining undifferentiated cells from the adipose tissue-derived cells;

(37) the method according to (36), which further comprises the step of forming a pancreatic islet from prepancreatic endocrine cells;

(38) the method according to (37), which comprises the steps (a) to (e):

(a) obtaining the undifferentiated cells from the adipose tissue-derived cells, (b) differentiating the undifferentiated cells to pancreatic precursor cells, (c) differentiating the pancreatic precursor cells to pancreatic endocrine precursor cells, (d) differentiating the pancreatic endocrine precursor cells to the prepancreatic endocrine cells, and (e) forming the pancreatic islet from the prepancreatic endocrine cells;

(39) the method according to any one of (36) to (38), wherein the step of obtaining the undifferentiated cells from the adipose tissue-derived cells is the step of culturing the adipose tissue-derived cells in suspended state to form adipospheres;

(40) the method according to any one of (37) to (39), wherein the step of forming the pancreatic islet from the prepancreatic endocrine cells is the step of differentiating the prepancreatic endocrine cells to the pancreatic endocrine cells and forming the pancreatic islet from the pancreatic endocrine cells;

(41) the method according to any one of (35) to (40), wherein the pancreatic islet contains the pancreatic endocrine cells;

(42) the method according to (41), wherein the pancreatic endocrine cells are insulin-secreting cells;

(43) a pancreatic islet which is obtainable by the method according to any one of (35) to (42);

(44) pancreatic endocrine cells which are contained in the pancreatic islet according to (43);

(45) the cells according to (44), which are insulin-secreting cells;

(46) a method for treatment or prevention of diseases caused by decrease in the function of pancreatic endocrine cells, which comprises administering pancreatic islets which are obtainable by the method according to any one of (35) to (42) to a subject;

(47) the method according to (46), wherein the pancreatic islet contains pancreatic endocrine cells;

(48) the method according to (47), wherein the pancreatic endocrine cells are insulin-secreting cells;

(49) the method according to any one of (46) to (48), wherein the disease is diabetes;

(50) a method for screening a substance which promotes formation of a pancreatic islet, which comprises, when culturing adipose tissue-derived cells to obtain the pancreatic islet, adding a candidate substance to a culture medium, wherein promoted formation of the pancreatic islet compared with formation in a medium without the candidate substance indicates that the candidate substance is a substance which promotes formation of a pancreatic islet;

(51) the method according to (50), wherein the pancreatic islet contains pancreatic endocrine cells;

(52) the method according to (51), wherein the pancreatic endocrine cells are insulin-secreting cells;

(53) a substance which promotes formation of a pancreatic islet, which is obtainable by the method according to any one of (50) to (52);

(54) a method for screening a substance which suppresses formation of a pancreatic islet, which comprises, when culturing adipose tissue-derived cells to obtain the pancreatic islet, adding a candidate substance to a culture medium, wherein suppressed formation of the pancreatic islet compared with formation in a medium without the candidate substance indicates that the candidate substance is a substance which suppresses formation of pancreatic islet;

(55) the method according to (54), wherein the pancreatic islet contains pancreatic endocrine cells;

(56) the method according to (55), wherein the pancreatic endocrine cells are insulin-secreting cells;

(57) a substance which suppresses formation of a pancreatic islet, which is obtainable by the method according to any one of (54) to (56);

(58) a kit for screening a substance which promotes or suppresses formation of a pancreatic islet, which is used in the method according to any one of (50) to (52) or (54) to (56);

(59) a method for screening a substance which increases activity of a pancreatic islet, which comprises, culturing pancreatic islets obtained by culturing adipose tissue-derived cells in a culture medium with a candidate substance, wherein difference of the amount of a substance secreted from the pancreatic islets compared with the amount in a medium without the candidate substance indicates that the candidate substance is a substance which increases activity of a pancreatic islet;

(60) the method according to (59), wherein the substance secreted from the pancreatic islets is insulin, C-peptide, glucagon, somatostatin, or pancreatic peptide;

(61) the method according to (59) or (60), wherein the pancreatic islet contains pancreatic endocrine cells;

(62) the method according to (61), wherein the pancreatic endocrine cells are insulin-secreting cells;

(63) a substance which increases activity of a pancreatic islet, which is obtainable by the method according to any one of (59) to (62);

(64) a method for screening a substance which decreases activity of a pancreatic islet, which comprises, culturing pancreatic islets obtained by culturing adipose tissue-derived cells in a culture medium with a candidate substance, wherein difference of the amount of a substance secreted from the pancreatic islets compared with the amount in a medium without the candidate substance indicates that the candidate substance is a substance which decreases activity of a pancreatic islet;

(65) the method according to (64), wherein the substance secreted from the pancreatic islets is insulin, C-peptide, glucagon, somatostatin, or pancreatic peptide;

(66) the method according to (64) or (65), wherein the pancreatic islet contains pancreatic endocrine cells;

(67) the method according to (66), wherein the pancreatic endocrine cells are insulin-secreting cells;

(68) a substance which decreases activity of a pancreatic islet, which is obtainable, by the method according to any one of (64) to (67);

(69) a kit for screening a substance which increases or decreases activity of a pancreatic islet, which is used in the method according to any one of (59) to (62) or (64) to (67);

(70) a method for obtaining undifferentiated cells from adipose tissue-derived cells, which comprises culturing the adipose tissue-derived cells;

(71) the method according to (70), wherein the culturing is the step of culturing the adipose tissue-derived cells in suspended state to form adipospheres;

(72) undifferentiated cells which are obtainable by the method according to (70) or (71);

(73) a method for treatment or prevention of diseases caused by decrease in the function of pancreas, liver, or heart, which comprises administering undifferentiated cells which are obtainable by the method according (70) or (71) to a subject;

(74) a method for obtaining pancreatic precursor cells from adipose tissue-derived cells, which comprises culturing the adipose tissue-derived cells;

(75) the method according to (74), which comprises the steps (a) and (b):
(a) obtaining undifferentiated cells from the adipose tissue-derived cells, and
(b) differentiating the undifferentiated cells to the pancreatic precursor cells;

(76) the method according to (75), wherein the step of obtaining the undifferentiated cells from the adipose tissue-derived cells is the step of culturing the adipose tissue-derived cells in suspended state to form adipospheres;

(77) pancreatic precursor cells which are obtainable by the method according to any one of (74) to (76);

(78) a method for treatment or prevention of diseases caused by decrease in the function of pancreas, which comprises transplanting pancreatic precursor cells which are obtainable by the method according to any one of (74) to (76) to a subject;

(79) a method for screening a substance which promotes or suppresses differentiation to pancreatic precursor cells, which comprises, when culturing adipose tissue-derived cells to obtain the pancreatic precursor cells, adding a candidate substance to a culture medium, wherein promoted or suppressed differentiation to the pancreatic precursor cells compared with the differentiation in a medium without the candidate substance indicates that the candidate substance is a substance which promotes or suppresses differentiation to pancreatic precursor cells;

(80) a substance which promotes or suppresses differentiation to pancreatic precursor cells, which is obtainable by the method according to (79);

(81) a kit for screening a substance which, promotes or suppresses differentiation to pancreatic precursor cells, which is used in the method according to (79);

(82) a method for obtaining pancreatic endocrine precursor cells from adipose tissue-derived cells, which comprises culturing the adipose tissue-derived cells;

(83) the method according to (82), which comprises the steps (a) to (c):
(a) obtaining undifferentiated cells from the adipose tissue-derived cells,
(b) differentiating the undifferentiated cells to pancreatic precursor cells, and
(c) differentiating the pancreatic precursor cells to the pancreatic endocrine precursor cells;

(84) the method according to (83), wherein the step of obtaining the undifferentiated cells from the adipose tissue-derived cells is the step of culturing the adipose tissue-derived cells in suspended state to form adipospheres;

(85) pancreatic precursor cells which are obtainable by the method according to any one of (82) to (84);

(86) a method for treatment or prevention of diseases caused by decrease in the function of pancreatic endocrine cells, which comprises administering the pancreatic precursor cells which are obtainable by the method according to any one of (82) to (84) to a subject;

(87) a method for screening a substance which promotes or suppresses differentiation to pancreatic endocrine precursor cells, which comprises, when culturing adipose tissue-derived cells to obtain the pancreatic endocrine precursor cells, adding a candidate substance to a culture medium, wherein promoted or suppressed differentiation to the pancreatic endocrine precursor cells compared with differentiation in a medium without the candidate substance indicates that the candidate substance is a substance which promotes or suppresses differentiation to pancreatic endocrine precursor cells;

(88) a substance which promotes or suppresses differentiation to pancreatic endocrine precursor cells, which is obtainable by the method according to (87);

(89) a kit for screening a substance which promotes or suppresses differentiation to pancreatic endocrine precursor cells, which is used in the method according to (87);

(90) a method for obtaining prepancreatic endocrine cells from adipose tissue-derived cells, which comprises culturing the adipose tissue-derived cells;

(91) the method according to (90), which comprises the steps (a) to (d):
(a) obtaining undifferentiated cells from the adipose tissue-derived cells,
(b) differentiating the undifferentiated cells to pancreatic precursor cells,
(c) differentiating the pancreatic precursor cells to pancreatic endocrine precursor cells, and
(d) differentiating the pancreatic endocrine precursor cells to the prepancreatic endocrine cells;

(92) the method according to (91), wherein the step of obtaining the undifferentiated cells from the adipose tissue-derived cells is the step of culturing the adipose tissue-derived cells in suspended state to form adipospheres;

(93) prepancreatic endocrine cells which are obtainable by the method according to any one of (90) to (92);

(94) a method for treatment or prevention of diseases caused by decreases in the function of pancreatic endocrine cells, which comprises administering prepancreatic endocrine cells which are obtainable by the method according to any one of (90) to (92) to a subject;

(95) a method for screening a substance which promotes or suppresses differentiation to prepancreatic endocrine cells, which comprises, when culturing adipose tissue-derived cells to obtain the prepancreatic endocrine cells, adding a candidate substance to a culture medium, wherein promoted or suppressed differentiation to the prepancreatic endocrine cells compared with differentiation in a medium without the candidate substance indicates that the candidate substance is a substance which promotes or suppresses differentiation to prepancreatic endocrine cells;

(96) a substance which promotes or suppresses differentiation to prepancreatic endocrine cells, which is obtainable by the method according to (95);

(97) a kit for screening a substance which promotes or suppresses differentiation to prepancreatic endocrine cells, which is used in the method according to (95).

EFFECTS OF THE INVENTION

The present invention provides a method for obtaining pancreatic endocrine cells from adipose tissue-derived cells, pancreatic endocrine cells which are obtainable by the method, a method for treatment or prevention of diseases caused by decrease in the function of pancreatic endocrine cells using the pancreatic endocrine cells, a method for screening a substance which promotes or suppresses differentiation to pancreatic endocrine cells, a kit for the method and the like. According to a preferable aspect of the present invention, the pancreatic endocrine cells can be obtained from the tissue or the cell derived from the same species or the same individual. Therefore the various problems described above can be solved.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
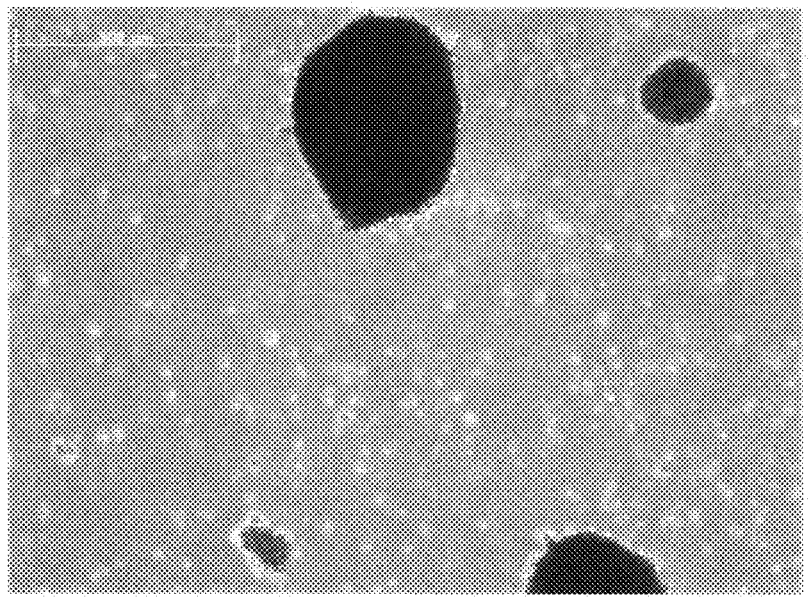
FIG. 1 is a microscope image of adipospheres formed by culturing adipose tissue-derived cells in suspended state. A scale bar indicates 502 μm.

In one aspect, the present invention relates to a method for obtaining pancreatic endocrine cells from adipose tissue-derived cells, which comprises culturing the adipose tissue-derived cells. The present invention has a great advantage of obtaining pancreatic endocrine cells without recombination but mainly by designing culture conditions including composition of the culture medium. An adipose tissue-derived cell refers to a cell or a cell population obtained from a visceral adipose tissue or a subcutaneous adipose tissue. Usually, an adipose tissue-derived cell refers to an adipose tissue-derived stem cell, an adipose tissue-derived interstitial cell, an adipose precursor cell, or a cell similar thereto or a cell population including a mixture of all or part thereof. The adipose tissue-derived cell can be obtained from an adipose tissue and the like by means or methods known to the person skilled in the art. The obtained adipose tissue-derived cell may be proliferated by means or methods known to the person skilled in the art, for example, to stabilize its trait. The adipose tissue-derived cell may be proliferated by culturing in a culture medium containing dexamethasone and ascorbic acid, for example, culturing in a culture medium containing 60% DMEM (low glucose), 40% MCDB201, ITS (10.0 ng/L insulin, 5.5 mg/L transferrin, 6.7 mg/mL of sodium selenite), 10 ng/mL EGF, 1 nM dexamethasone, 0.1 mM ascorbic acid, and 5% FCS in a culture container such as a fibronectin coated dish.

The animal species from which the adipose tissue-derived cell is derived is not specifically limited. For example, a mammal such as a mouse, rat, rabbit, dog, cat, bovine, horse and monkey is preferable, and human is more preferable. It is more preferable to use an adipose tissue-derived cell from the same species or the same individual as an animal with disease to be treated or prevented. Because an adipose tissue exists in sufficient amount in the living body and is obtained relatively readily, the present invention has an advantage compared with the method for obtaining a pancreatic islet from the limited material such as corpse. For example, it becomes possible to treat diabetes without being apprehensive about rejection by practicing the method of the present invention with self-adipose tissue-derived cells, and autologous transplantation of the obtained pancreatic endocrine cells.

An pancreatic endocrine cell refers to an endocrine cell such as an insulin-secreting cell, glucagon-secreting cell, somatostatin-secreting cell and pancreatic peptide-secreting cell, which constructs a pancreatic islet, and a cell which has a function or a form similar thereto. In the present invention, the pancreatic endocrine cells may form a pancreatic islet.

The method for obtaining pancreatic endocrine cells from adipose tissue-derived cells of the present invention preferably comprises the step of obtaining undifferentiated cells from the adipose tissue-derived cells (step (a) below) as its important step. An undifferentiated cell refers to a cell which can be differentiated to various cells, for example, pancreatic precursor cells, hepatic precursor cells, and cardiac precursor cells. The step of obtaining the undifferentiated cells may further comprise the step of proliferating the obtained undifferentiated cells. Proliferating the undifferentiated cells allows to increase the efficiency of the differentiation to the pancreatic endocrine cells, and increase the number of the obtained pancreatic endocrine cells. The step of obtaining the undifferentiated cells may be carried out using known methods, for example, a method with an antigen-antibody reaction including sorting method, MACS and rosetta formation method, density gradient method, selection method depending on the form and single cell cloning, or carried out by culturing the adipose tissue-derived cells in suspended state to form adipospheres. Culture the adipose tissue-derived cells in suspended state to form adipospheres is preferable, because it can kill the cells which have been already differentiated and maintain and proliferate the undifferentiated cells. In the present specification, an adiposphere is defined as a sphere which contains undifferentiated cells as its main component. Because the formation of the adiposphere and the following differentiation to the pancreatic precursor cells may occur sequentially or simultaneously, the adiposphere may contain pancreatic precursor cells in addition to the undifferentiated cells.

Culturing the adipose tissue-derived cells as described above means culturing the cells keeping them in the isolated state by preventing or suppressing adhesion or agglutination thereof with a culture container or other cells. The suspension of the cells can be performed by various known means or methods. For example, cells may be suspended using a culture container or apparatus which has been treated so that adhesion of cells might be prevented or suppressed, or is made from a material which prevents or suppresses adhesion of cells. The culture containers or apparatuses include a silicone-treated culture container (for example, silicone-treated flask) and a low attachment culture container such as a low attachment culture dish (for example, Hydrocell (CellSeed Inc.)). Alternatively, cells may be cultured in the suspended state using the hanging drop culture method. At the start of the suspension or in order to keep the suspended state, known means or methods may also be used appropriately. Examples of the means or methods include separating cells by an enzyme or chelating agent such as trypsin/ethylenediaminetetraacetic acid (EDTA), collagenase and Cell Dissociation Buffer (GIBCO Invitrogen), physically collecting cells using a scraper and the like, and a method which comprises culturing cells in temperature-responsive cell cultureware for cell collection (for example, RepCell (CellSeed)) and separating the cells by incubation, for example, at 20° C. for 30 minutes. By culturing the adipose tissue-derived cells in the suspended state, the adiposphere as described above is formed.

Preferably, the method for obtaining the pancreatic endocrine cells from the adipose tissue-derived cells of the present invention further comprises the step of differentiating prepancreatic endocrine cells to the pancreatic endocrine cells (step (e) below) as its important step.

Furthermore, the method of the present invention as described above may comprise the steps (a) to (e):

(a) obtaining the undifferentiated cells from the adipose tissue-derived cells, (b) differentiating the undifferentiated cells to pancreatic precursor cells, (c) differentiating the pancreatic precursor cells to pancreatic endocrine precursor cells, (d) differentiating the pancreatic endocrine precursor cells to the prepancreatic endocrine cells, and (e) differentiating the prepancreatic endocrine cells to the pancreatic endocrine cells.

A pancreatic precursor cell is a cell which is obtainable from an undifferentiated cell and has an ability to differentiate to a pancreatic endocrine precursor cell and a pancreatic exocrine precursor cell. Induction of the pancreatic precursor cells from the undifferentiated cells can be carried out by culturing the undifferentiated cells using means or methods known to the person skilled in the art. For example, the pancreatic precursor cells may be induced by culturing the undifferentiated cells in a culture medium containing DMEM/F-12 (1:1), ITS (10 mg/L insulin, 6.7 mg/L transferrin and 5.5 mg/L selenium), 1 mM glutamine and 5 μg/mL human fibronectin in a plastic culture plate.

A pancreatic endocrine precursor cell is a cell which is obtainable from a pancreatic precursor cell and has an ability to differentiate to a prepancreatic endocrine cell. Differentiation to the pancreatic endocrine precursor cells from pancreatic precursor cells can be carried out by culturing pancreatic precursor cells using means or methods known to the person skilled in the art. For example, the pancreatic precursor cells may be differentiated to the pancreatic endocrine precursor cells by culturing the pancreatic precursor cells in a culture medium containing DMEM/F-12(1:1), N2 (GIBCO Invitrogen), B27 (GIBCO Invitrogen), 1 mM glutamine and 10 ng/mL bFGF in a 0.1% gelatin coated plastic tissue culture plate.

A prepancreatic endocrine cell is a cell which is obtainable from a pancreatic endocrine precursor cell and is committed to a pancreatic endocrine cell such as an insulin-secreting cell, glucagon-secreting cell, somatostatin-secreting cell, and a pancreatic peptide-secreting cell. Specifically, it is a cell in which an insulin gene, glucagon gene, somatostatin gene, or pancreatic peptide gene is not expressed, but transcription factors such as PDX-1, Islet-1, Pax4 and Pax6, nestin or the like is expressed. Such prepancreatic endocrine cell is a cell which can be obtained in the step of differentiation of the pancreatic endocrine precursor cell to the pancreatic endocrine cell in the method of the present invention. The differentiation of the pancreatic endocrine precursor cells to the prepancreatic endocrine cells can be carried out by culturing the pancreatic endocrine precursor cells using means or methods known to the person skilled in the art. For example, the pancreatic endocrine precursor cells may be differentiated to the prepancreatic endocrine cells by culturing the pancreatic endocrine precursor cells in a culture medium containing exendin-4, for example, a culture medium containing DMEM (without glucose)/F-12 (1:1), N2 and B27, 1 mM glutamine, 10 mM nicotinamide and 10 nM exendin-4.

The differentiation of the prepancreatic endocrine cells to the pancreatic endocrine cells can be carried out by means or methods known to the person skilled in the art. For example, the prepancreatic endocrine cells may be differentiated to the pancreatic endocrine cells by culturing in a culture medium containing DMEM (without glucose)/F-12 (1:1), N2 and B27, 1 mM glutamine, 10 mM nicotinamide and 10 nM exendin-4 in a low attachment culture dish.

As described above, the obtained pancreatic endocrine cells may form a pancreatic islet. The pancreatic islet is formed by culturing cells in the suspended state in differentiating the prepancreatic endocrine cells to the pancreatic endocrine cells, or after differentiating the prepancreatic endocrine cells to the pancreatic endocrine cells.

In another aspect, the present invention relates to pancreatic endocrine cells which are obtainable by the method as described above. For example, by practicing the method as described above using cells collected from the adipose tissue derived from the subject with diabetes or the predisposition thereof or the same species as that of the subject, and transplanting the obtained pancreatic endocrine cells to the subject, it is possible to treat or prevent diabetes. The pancreatic endocrine cells according to this aspect of the present invention may form a pancreatic islet as described above.

In another aspect, the present invention relates to a method for treatment or prevention of diseases caused by decrease in the function of pancreatic endocrine cells, which comprises administering the pancreatic endocrine cells obtainable by the method for culturing as described above to a subject. The diseases caused by decreases in the function of the pancreatic endocrine cells include a disease caused by not only decreased function but also dysfunction of the pancreatic endocrine cells, for example, diabetes and diseases induced thereby, pancreatic cancer postoperative diabetes, hyperlipidemia, pancreatic cyst, chronic pancreatitis, and sequela of acute pancreatitis. The diseases induced by diabetes include a disease induced by persistence of hyperglycemia such as neuropathy, retinopathy, nephropathy, atherosclerotic disease, arteriosclerotic disease, coronary artery disease including myocardial infarction and the like, and cerebrovascular disorder. Taking problems such as rejection into consideration, it is preferable to use the pancreatic endocrine cells which are obtainable from the adipose tissue-derived cells derived from the same species or autologous cells. The means or method of the administration can be appropriately selected depending on various factors. For example, the pancreatic endocrine cells may be injected to the portal vein in the subject, be transplanted under renal capsule, or be transplanted subcutaneously or intramuscularly. The dose, number of times or the like of the administration is appropriately selected depending on various factors such as the condition of the subject and the severity of the disease.

In another aspect, the present invention relates to a method for screening a substance which promotes differentiation to pancreatic endocrine cells, which comprises, when culturing adipose tissue-derived cells to obtain the pancreatic endocrine cells, adding a candidate substance to a culture medium, wherein promoted differentiation to the pancreatic endocrine cells compared with differentiation in a medium without the candidate substance indicates that the candidate substance is a substance which promotes differentiation to pancreatic endocrine cells.

Examples of the candidate substances include, but are not limited to, various substances such as analogs of GLP-1 or exendin-4, and derivatives and variants thereof.

Addition of the candidate substance to the culture medium in obtaining the pancreatic endocrine cells from the adipose tissue-derived cells may be carried out once, or two or more times in any stage. The candidate substance may be added to the culture medium, for example, in obtaining the undifferentiated cells from the adipose tissue-derived cells, differentiating the undifferentiated cells to the pancreatic precursor cells, differentiating the pancreatic precursor cells to the pancreatic endocrine precursor cells, differentiating the pancreatic endocrine precursor cells to the prepancreatic endocrine cells, and/or differentiating the prepancreatic endocrine cells to the pancreatic endocrine cells.

The differentiation to the pancreatic endocrine cells can be examined, for example, by counting the number of the induced pancreatic endocrine cells under the microscopic observation, by quantifying insulin, C-peptide, glucagon, somatostatin, or pancreatic peptide secreted to the culture supernatant, for example, with ELISA, by determining the expression of an insulin gene, glucagon gene, somatostatin gene, or a pancreatic peptide gene with quantitative PCR, or by determining a marker which is known for the decrease or increase of its expression with the differentiation to the pancreatic endocrine cells, for example, IAPP, Pdx-1, Islet-1, Nkx6.1, PC1/3, and PC2 with quantitative PCR, ELISA or the like. Also, it may be examined indirectly by examining the differentiation of the undifferentiated cells to the pancreatic precursor cells, the differentiation of the pancreatic precursor cells to the pancreatic endocrine precursor cells, the differentiation of the pancreatic endocrine precursor cells to the prepancreatic endocrine cells, or the differentiation of the prepancreatic endocrine cells to the pancreatic endocrine cells. The person skilled in the art can select and use appropriately the means or method for examining the differentiation of the undifferentiated cells to the pancreatic precursor cells, the differentiation of the pancreatic precursor cells to the pancreatic endocrine precursor cells, the differentiation of the pancreatic endocrine precursor cells to the prepancreatic endocrine cells, or the differentiation of the prepancreatic endocrine cells to the pancreatic endocrine cells.

Thus, in a further aspect, the present invention relates to a substance which promotes differentiation to pancreatic endocrine cells, which is obtainable by the method for screening as described above. Such substance may be used in the method for obtaining the pancreatic endocrine cells from the adipose tissue-derived cells of the present invention to increase the number of the obtained pancreatic endocrine cells, or to increase the rate of the differentiation to the pancreatic endocrine cells. Such substance may also be used for treatment or prevention of diseases caused by decreases in the function of the pancreatic endocrine cells.

Another aspect of the present invention is a method for screening a substance which suppresses differentiation to pancreatic endocrine cells. That is, in the method for screening as described above, the suppressed differentiation to the pancreatic endocrine cells in the presence of the candidate substance indicates that the candidate substance is a substance which suppresses differentiation to pancreatic endocrine cells. Examples of the candidate substances include, but are not limited to, various substances such as analogs, derivatives, and variants of steroid hormones. It is considered that the substance obtainable by the method for screening is appropriate for treatment or prevention of diseases caused by increase in the function of the pancreatic endocrine cells, for example, pancreatic hyperfunction and insulinoma.

Thus, in a further aspect, the present invention relates to a substance which suppresses differentiation to pancreatic endocrine cells, which is obtainable by the method for screening as described above.

In another aspect, the present invention relates to a kit for screening a substance which promotes or suppresses differentiation to pancreatic endocrine cells, which is used in the methods for screening as described above. The kit of the present invention may comprise means to obtain cells from an adipose tissue, a culture medium, a culture container, and means to examine the differentiation to the pancreatic endocrine cells. In general, an instruction manual is attached to the kit. By using the kit of the present invention, the methods for screening as described above can be carried out rapidly and readily.

In another aspect, the present invention relates to a method for screening a substance which increases activity of pancreatic endocrine cells, which comprises, culturing the pancreatic endocrine cells obtained by culturing adipose tissue-derived cells in a culture medium with a candidate substance, wherein the difference of the amount of a substance secreted from the pancreatic endocrine cells compared with the amount in a medium without the candidate substance indicates that the candidate substance is a substance which increases activity of pancreatic endocrine cells. The activity of the pancreatic endocrine cells refers to an action of producing and secreting insulin, C-peptide, glucagon, somatostatin, pancreatic peptide and the like, and the glucose response of the pancreatic endocrine cells, specifically, an action of adjusting the secreted amount of insulin, C-peptide, glucagon, somatostatin, pancreatic peptide or the like depending on the level of glucose. The substance secreted from the pancreatic endocrine cells refers to, for example, insulin, C-peptide, glucagon, somatostatin, or pancreatic peptide. The difference of the amount of the substance refers to increase when the substance is increased with increasing the activity of the pancreatic endocrine cells, and decrease when the substance is decreased with decreasing the activity of the pancreatic endocrine cells.

Increasing the activity of the pancreatic endocrine cells can be examined, for example, by quantifying insulin, C-peptide, glucagon, somatostatin, or pancreatic peptide secreted to the culture supernatant, for example, with ELISA, or by determining the expression of an insulin gene, glucagon gene, somatostatin gene, or pancreatic peptide gene with quantitative PCR. Examples of the candidate substances include, but are not limited to, various substances such as analogs, derivatives or variants of theophylline, IBMX, tolbutamide, or carbachol.

Thus, in a further aspect, the present invention relates to a substance which increases activity of pancreatic endocrine cells, which is obtainable by the method for screening as described above. Such substance may be used for treatment or prevention of diseases caused by decreases in the function of the pancreatic endocrine cells.

Another aspect of the present invention is a method for screening a substance which decreases activity of pancreatic endocrine cells. That is, in the method for screening as described above, the decreased activity in the presence of the candidate substance indicates that the candidate substance is a substance which decreases activity of pancreatic endocrine cells. Examples of the candidate substances include, but are not limited to, various substances, for example, Ca blockers such as nifedipine or analogs, derivatives, or variants thereof. It is considered that the substance obtainable by the method for screening is appropriate for treatment or prevention of diseases caused by increase in the function of the pancreatic endocrine cells, such as pancreatic hyperfunction and insulinoma.

Thus, in a further aspect, the present invention relates to a substance which decreases activity of pancreatic endocrine cells, which is obtainable by the method for screening as described above.

In another aspect, the present invention relates to a kit for screening a substance which increases or decreases activity of pancreatic endocrine cells, which is used in the methods for screening as described above. The kit of the present invention may comprise a culture medium or a culture container to culture the pancreatic endocrine cells, means to examine the activity of the pancreatic endocrine cells or the like. In general, an instruction manual is attached to the kit. By using the kit of the present invention, the methods for screening as described above can be carried out rapidly and readily.

In another aspect, the present invention relates to a method for obtaining a pancreatic islet from adipose tissue-derived cells, which comprises culturing the adipose tissue-derived cells. The present invention has a great advantage of obtaining a pancreatic islet without recombination but mainly by designing culture conditions including composition of the culture medium.

The pancreatic islet refers to a pancreatic islet in a living body, or a mass of cells, which has the function and form similar thereto, and contains, for example, a pancreatic endocrine cell such as an insulin-secreting cell, a glucagon-secreting cell, a somatostatin-secreting cell and a pancreatic peptide-secreting cell, and a cell having the function similar thereto. Thus, the method of this aspect of the present invention encompasses obtaining the pancreatic endocrine cells contained in the pancreatic islet, and the insulin-secreting cell, the glucagon-secreting cell, the somatostatin-secreting cell, the pancreatic peptide-secreting cell and the like which are one of the pancreatic endocrine cells. The pancreatic islet of the present invention has an advantage that it can produce and secrete the sufficient amount of insulin, glucagon, somatostatin, pancreatic peptide and the like compared with those in the individual cell. Additionally, it can be transplanted readily into a living body using the known method for transplanting an pancreatic islet.

The method for obtaining the pancreatic islet from the adipose tissue-derived cells of the present invention preferably comprises the step of obtaining undifferentiated cells from the adipose tissue-derived cells (step (a) below) as its important step.

Preferably, the method for obtaining the pancreatic endocrine cells from the adipose tissue-derived cells of the present invention further comprises the step of forming the pancreatic islet from prepancreatic endocrine cells (the step (e) below) as its important step.

Furthermore, the method of the present invention may comprise the steps (a) to (e):

(a) obtaining the undifferentiated cells from the adipose tissue-derived cells, (b) differentiating the undifferentiated cells to pancreatic precursor cells, (c) differentiating the pancreatic precursor cells to pancreatic endocrine precursor cells, (d) differentiating the pancreatic endocrine precursor cells to the prepancreatic endocrine cells, and (e) forming the pancreatic islet from the prepancreatic endocrine cells.

The step of obtaining the undifferentiated cells from adipose tissue-derived cells, the step of differentiating the undifferentiated cells to the pancreatic precursor cells, the step of differentiating the pancreatic precursor cells to the pancreatic endocrine precursor cells, and the step of differentiating the pancreatic endocrine precursor cells to the prepancreatic endocrine cells are described above.

The formation of the pancreatic islet from the prepancreatic endocrine cells can be performed using means or method known to the person skilled in the art, preferably, by culturing the prepancreatic endocrine cells in suspended state to form the pancreatic islet. The suspension is described above. For example, the pancreatic islet may be formed by culturing the prepancreatic endocrine cells in a culture medium containing DMEM (without glucose)/F-12 (1:1), N2 and B27, 1 mM glutamine, 10 mM nicotinamide, and 10 nM exendin-4 in a low attachment culture dish. The pancreatic islet may also be formed from the pancreatic endocrine cells after differentiating the prepancreatic endocrine cells to the pancreatic endocrine cells.

In another aspect, the present invention relates to a pancreatic islet which is obtainable by the method as described above. For example, by practicing the method as described above using cells collected from the adipose tissue derived from the subject with diabetes or the predisposition thereof or the same species as that of the subject and transplanting the obtained pancreatic islet to the subject, it is possible to treat or prevent diabetes. As described above, the pancreatic islet according to this aspect of the present invention contains the pancreatic endocrine cells. Thus, this aspect of the present invention also relates to the pancreatic endocrine cells contained in the pancreatic islet which is obtainable by the above method, for example, insulin-secreting cells, glucagon-secreting cells, somatostatin secreting-cells, and pancreatic peptide-secreting cells.

In another aspect, the present invention relates to a method for treatment or prevention of diseases caused by decrease in the function of pancreatic endocrine cells, which comprises administering pancreatic islets which are obtainable by the method for obtaining as described above to a subject. Because the pancreatic islets which are obtainable by the method for obtaining as described above contain the pancreatic endocrine cells, administering the pancreatic islets to the subject encompasses administering the pancreatic endocrine cells, and the insulin-secreting cells, the glucagon-secreting cells, the somatostatin-secreting cells, the pancreatic peptide-secreting cells and the like which are one of the pancreatic endocrine cells. Taking problems such as rejection into consideration, it is preferable to use the pancreatic islets which are obtainable from the adipose tissue-derived cells derived from the same species or self-derived cells. The means or method of the administration can be appropriately selected depending on various factors. For example, the pancreatic islets may be injected to the portal vein in the subject, be transplanted under renal capsule, or be transplanted subcutaneously or intramuscularly. The dose, number of times or the like of the administration of the pancreatic islets is appropriately selected depending on various factors such as the condition of the subject and the severity of the disease.

In another aspect, the present invention relates to a method for screening a substance which promotes formation of a pancreatic islet, which comprises, when culturing the adipose tissue-derived cells to obtain the pancreatic islet, adding a candidate substance to a culture medium, wherein promoted differentiation to the pancreatic islets compared with formation in a medium without the candidate substance indicates that the candidate substance is a substance which promotes formation of a pancreatic islet.

Examples of the candidate substances include, but are not limited to, various substances such as analogs of GLP-1 or exendin-4, and derivatives and variants thereof.

Addition of the candidate substance to the culture medium in obtaining the pancreatic islets from the adipose tissue-derived cells may be carried out once, or two or more times in any stage. The candidate substance may be added to the culture medium, for example, in differentiating the undifferentiated cells to the pancreatic precursor cells, differentiating the pancreatic precursor cells to the pancreatic endocrine precursor cells, differentiating the pancreatic endocrine precursor cells to the prepancreatic endocrine cells, and/or forming the pancreatic islets from the prepancreatic endocrine cells.

The formation of the pancreatic islets can be examined, for example, by counting the number of the formed pancreatic islets under the microscopic observation, by quantifying insulin, C-peptide, glucagon, somatostatin, or pancreatic peptide secreted to the culture supernatant, for example, with ELISA, by determining the expression of an insulin gene, glucagon gene, somatostatin gene, or pancreatic peptide gene with quantitative PCR, or by determining a marker which is known for the decrease or increase of its expression with the formation of the pancreatic islets, for example, IAPP, Pdx-1, Islet-1, Nkx6.1, PC1/3, and PC2 with quantitative PCR, ELISA or the like. Also, it may be examined indirectly by examining the differentiation of the undifferentiated cells to the pancreatic precursor cells, the differentiation of the pancreatic precursor cells to the pancreatic endocrine precursor cells, the differentiation of the pancreatic endocrine precursor cells to the prepancreatic endocrine cells, or the formation of the pancreatic islets from the prepancreatic endocrine cells. The person skilled in the art can select and use appropriately the means or method for examining the differentiation of the undifferentiated cells to the pancreatic precursor cells, the differentiation of the pancreatic precursor cells to the pancreatic endocrine precursor cells, the differentiation of the pancreatic endocrine precursor cells to the prepancreatic endocrine cells, or the formation of the pancreatic islets from the prepancreatic endocrine cells.

Thus, in a further aspect, the present invention relates to a substance which promotes formation of a pancreatic islet, which is obtainable by the method for screening as described above. Such substance may be used in the method for obtaining the pancreatic islet from adipose tissue-derived cells of the present invention to increase the number of the obtained pancreatic islets, or to increase the rate of the formation of the pancreatic islets. Such substance may also be used for treatment or prevention of diseases caused by decreases in the function of the pancreatic endocrine cells.

Another aspect of the present invention is a method for screening a substance which suppresses formation of a pancreatic islet. That is, in the method for screening as described above, the suppressed formation of the pancreatic islets in the presence of the candidate substance indicates that the candidate substance is a substance which suppresses formation of a pancreatic islet. Examples of the candidate substances include, but are not limited to, various substances such as analogs, derivatives, and variants of steroid hormones. It is considered that the substance obtainable by the method for screening is appropriate for treatment or prevention of diseases caused by increase in the function of the pancreatic endocrine cells, for example, pancreatic hyperfunction and insulinoma.

Thus, in a further aspect, the present invention relates to a substance which suppresses formation of a pancreatic islet, which is obtainable by the method for screening as described above.

In another aspect, the present invention relates to a kit for screening a substance which promotes or suppresses formation of pancreatic islet, which is used in the methods for screening as described above. The kit of the present invention may comprise means to obtain cells from an adipose tissue, a culture medium, a culture container, and means to examine the formation of the pancreatic islets. In general, an instruction manual is attached to the kit. By using the kit of the present invention, the methods for screening as described above can be carried out rapidly and readily.

In another aspect, the present invention relates to a method for screening a substance which increases activity of a pancreatic islet, which comprises, culturing the pancreatic islets obtained by culturing adipose tissue-derived cells in a culture medium with a candidate substance, wherein difference of the amount of a substance secreted from the pancreatic islets compared with the amount in a medium without the candidate substance indicates that the candidate substance is a substance which increases activity of a pancreatic islet. The activity of the pancreatic islet includes the activities of the pancreatic endocrine cell, insulin-secreting cell, glucagon-secreting cell, somatostatin secreting-cell, pancreatic peptide-secreting cell and the like, and refers to an action of producing and secreting insulin, C-peptide, glucagon, somatostatin, pancreatic peptide and the like, and the glucose response, specifically, an action of adjusting the secreted amount of insulin, C-peptide, glucagon, somatostatin, pancreatic peptide or the like depending on the level of glucose. The substance secreted from the pancreatic islets refers to, for example, insulin, C-peptide, glucagon, somatostatin, and pancreatic peptide. The difference of the amount of the substance refers to increase when the substance is increased with increasing the activity of the pancreatic islets, and decrease when the substance is decreased with decreasing the activity of the pancreatic islets.

Increasing the activity of the pancreatic islets can be examined, for example, by quantifying insulin, C-peptide, glucagon, somatostatin, or pancreatic peptide secreted to the culture supernatant, for example, with ELISA, or by determining the expression of an insulin gene, glucagon gene, somatostatin gene, or pancreatic peptide gene with quantitative PCR. Examples of the candidate substances include, but are not limited to, various substances such as analogs, derivatives or variants of theophylline, IBMX, tolbutamide, or carbachol.

Thus, in a further aspect, the present invention relates to a substance which increases activity of a pancreatic islet, which is obtainable by the method for screening as described above. Such substance may be used for treatment or prevention of diseases caused by decreases in the function of the pancreatic endocrine cells.

Another aspect of the present invention is a method for screening a substance which decreases activity of a pancreatic islet. That is, in the method for screening as described above, the decreased activity in the presence of the candidate substance indicates that the candidate substance is a substance which decreases activity of a pancreatic islet. Examples of the candidate substances include, but are not limited to, various substances, for example, Ca blockers such as nifedipine or analogs, derivatives, or variants thereof. It is considered that the substance obtainable by the method for screening is appropriate for treatment or prevention of diseases caused by increase in the function of the pancreatic endocrine cells, such as pancreatic hyperfunction and insulinoma.

Thus, in a further aspect, the present invention relates to a substance which decreases activity of a pancreatic islet, which is obtainable by the method for screening as described above.

In another aspect, the present invention relates to a kit for screening a substance which increases or decreases activity of a pancreatic islet, which is used in the methods for screening as described above. The kit of the present invention may comprise a culture medium or a culture container to culture the pancreatic islets, means to examine the activity of the pancreatic islets or the like. In general, an instruction manual is attached to the kit. By using the kit of the present invention, the methods for screening as described above can be carried out rapidly and readily.

In another aspect, the present invention relates to a method for obtaining undifferentiated cells from adipose tissue-derived cells, which comprises culturing the adipose tissue-derived cells. Preferably, the method above is practiced by culturing the adipose tissue-derived cells in suspended state to form adipospheres.

In a further aspect, the present invention relates to undifferentiated cells which are obtainable by the method as described above.

In a further aspect, the present invention relates to a method for treatment or prevention of diseases caused by decrease in the function of pancreas, liver, or heart, which comprises administering undifferentiated cells which are obtainable by the method for obtaining as described above to a subject. Examples of the diseases caused by decreases in the function of pancreas, liver, or heart include disease caused by decrease in the function of pancreatic endocrine cells, disease caused by decreases in the function of pancreatic exocrine cells such as chronic pancreatitis and pancreatic cysts, disease caused by decreases in the function of hepatocytes such as hepatic cirrhosis and hepatic cancer, diseases caused by decreases in the function of cardiomyocytes.

In another aspect, the present invention relates to a method for obtaining pancreatic precursor cells from adipose tissue-derived cells, which comprises culturing the adipose tissue-derived cells. Preferably, the method comprises the steps of obtaining undifferentiated cells from the adipose tissue-derived cells, and differentiating the undifferentiated cells to pancreatic precursor cells. The pancreatic precursor cells obtainable by the method can be differentiated to pancreatic endocrine precursor cells using the method as described above, and be differentiated to pancreatic exocrine precursor cells using means or method known to the person skilled in the art, for example, the method described in Skoudy A et al., Biochem J. 2004 May 1; 379 (Pt 3); 749-56. The obtained pancreatic precursor cells can also be confirmed, for example, by determining a marker such as CK18, CK19, amylase, and trypsin4.

In a further aspect, the present invention relates to a pancreatic precursor cell, which is obtainable by the method as described above. Because the pancreatic precursor cell has an ability to differentiate to not only a pancreatic endocrine precursor cell but also a pancreatic exocrine precursor cell, it is considered that the pancreatic precursor cell can be used for treatment or prevention of a wide variety of diseases, for example, pancreatic exocrine dysfunction including chronic pancreatitis and pancreatic cysts in addition to disease caused by decrease in the function of a pancreatic endocrine cell.

In a further aspect, the present invention relates to a method for treatment or prevention of diseases caused by decrease in the function of pancreas, which comprises transplanting pancreatic precursor cells which are obtainable by the method as described above. Examples of the diseases caused by decreases in the function of pancreas include a disease caused by decrease in the function of a pancreatic endocrine cell, and a disease caused by decrease in the function of a pancreatic exocrine cell. The disease caused by decrease in the function of a pancreatic exocrine cell includes a disease caused by dysfunction of a pancreatic exocrine cell such as chronic pancreatitis and pancreatic cysts. The dose, method, route, number of times of administration of the pancreatic precursor cell may be appropriately selected depending on various conditions such as the condition of the subject.

In a further aspect, the present invention relates to a method for screening a substance which promotes or suppresses differentiation to pancreatic precursor cells, which comprises, when culturing adipose tissue-derived cells to obtain the pancreatic precursor cells, adding a candidate substance to a culture medium, wherein promoted or suppressed differentiation to the pancreatic precursor cells compared with the differentiation in a medium without the candidate substance indicates that the candidate substance is a substance which promotes or suppresses differentiation to pancreatic precursor cells. The addition of the candidate substance to the culture medium is described above. The promoted or suppressed differentiation to the pancreatic precursor cells can be determined by various means or methods. For example, it may be determined by counting the number of pancreatic precursor cells, or examining the gene expressed or the protein produced by the pancreatic precursor cells.

In a further aspect, the present invention relates to a substance which promotes or suppresses differentiation to pancreatic precursor cells, which is obtainable by the method for screening as described above.

In a further aspect, the present invention relates to a kit for screening a substance which promotes or suppresses differentiation to pancreatic precursor cells, which is used in the method as described above. The components of the kit are described above.

In a further aspect, the present invention relates to a method for obtaining pancreatic endocrine precursor cells from adipose tissue-derived cells, which comprises culturing the adipose tissue-derived cells. Preferably, the method comprises the step of obtaining undifferentiated cells from the adipose tissue-derived cells, differentiating the undifferentiated cells to pancreatic precursor cells, and differentiating the pancreatic precursor cells to the pancreatic endocrine precursor cells. The pancreatic endocrine precursor cells obtainable by the method can be differentiated to prepancreatic endocrine cells, and pancreatic endocrine cells such as insulin-secreting cells, glucagon-secreting cells, somatostatin-secreting cells, and pancreatic peptide-secreting cells.

In a further aspect, the present invention relates to pancreatic endocrine precursor cells, which are obtainable by the method as described above. Because the pancreatic endocrine precursor cells can be differentiated to prepancreatic endocrine cells, and pancreatic endocrine cells such as insulin-secreting cells, glucagon-secreting cells, somatostatin-secreting cells, and pancreatic peptide-secreting cells, it can be used for treatment or prevention of diseases caused by decreases in the function of pancreatic endocrine cells.

In a further aspect, the present invention relates to a method for treatment or prevention of diseases caused by decrease in the function of pancreatic endocrine cells, which comprises administering pancreatic endocrine precursor cells which are obtainable by the method as described above. The dose, number of times, method or the like of administration of the pancreatic endocrine precursor cell is appropriately selected depending on various factors such as the condition of the subject.

In a further aspect, the present invention relates to a method for screening a substance which promotes or suppresses differentiation to pancreatic endocrine precursor cells, which comprises, when culturing adipose tissue-derived cells to obtain the pancreatic endocrine precursor cells, adding a candidate substance to a culture medium, wherein promoted or suppressed differentiation to the pancreatic endocrine precursor cells compared with differentiation in a medium without the candidate substance indicates that the candidate substance is a substance which promotes or suppresses differentiation to pancreatic precursor cells. The addition of the candidate substance is described above. The promoted or suppressed differentiation to the pancreatic endocrine precursor cells can be determined by various means or methods. For example, it may be determined by examining differentiation of the undifferentiated cells to the pancreatic precursor cells, or differentiation of the pancreatic precursor cells to the pancreatic endocrine precursor cells, or examining the gene expressed or the protein produced by the pancreatic endocrine precursor cells.

In a further aspect, the present invention relates to a substance which promotes or suppresses differentiation to the pancreatic endocrine precursor cells, which is obtainable by the method for screening as described above.

In a further aspect, the present invention relates to a kit for screening a substance which promotes or suppresses differentiation to the pancreatic endocrine precursor cells, which is used in the method as described above. The components of the kit are described above.

In another aspect, the present invention relates to a method for obtaining prepancreatic endocrine cells from adipose tissue-derived cells, which comprises culturing the adipose tissue-derived cells. Preferably, the method comprises the steps of obtaining undifferentiated cells from the adipose tissue-derived cells, differentiating the undifferentiated cells to pancreatic precursor cells, differentiating the pancreatic precursor cells to pancreatic endocrine precursor cells, and differentiating the pancreatic endocrine precursor cells to the prepancreatic endocrine cells.

In a further aspect, the present invention relates to prepancreatic endocrine cells, which are obtainable by the method as described above. Because the prepancreatic endocrine cells can be differentiated to insulin-secreting cells, glucagon-secreting cells, somatostatin-secreting cells, or pancreatic peptide-secreting cells, it can be used for treatment or prevention of diseases caused by decreases in the function of pancreatic endocrine cells.

In a further aspect, the present invention relates to a method for treatment or prevention of diseases caused by decrease in the function of pancreatic endocrine cells, which comprises administering prepancreatic endocrine cells which are obtainable by the method as described above to a subject. The dose, number of times, method or the like of administration of the prepancreatic endocrine cell is appropriately selected depending on various factors such as the condition of the subject.

In a further aspect, the present invention relates to a method for screening a substance which promotes or suppresses differentiation to prepancreatic endocrine cells, which comprises, when culturing adipose tissue-derived cells to obtain the prepancreatic endocrine cells, adding a candidate substance to a culture medium, wherein promoted or suppressed differentiation to the prepancreatic precursor cells compared with differentiation in a medium without the candidate substance indicates that the candidate substance is a substance which promotes or suppresses differentiation to prepancreatic precursor cells. The addition of the candidate substance is described above. The promoted or suppressed differentiation to the prepancreatic endocrine cells may be determined directly by measuring the expression of a gene such as PDX-1 and Islet-1 in the prepancreatic endocrine cells, or indirectly, for example, by examining differentiation of the undifferentiated cells to the pancreatic precursor cells, or differentiation of the pancreatic precursor cells to the pancreatic endocrine precursor cells.

In a further aspect, the present invention relates to a substance which promotes or suppresses differentiation to prepancreatic endocrine cells, which is obtainable by the method for screening as described above.

In a further aspect, the present invention relates to a kit for screening a substance which promotes or suppresses differentiation to prepancreatic endocrine cells, which is used in the method as described above. The components of the kit are described above.

The following examples illustrate the present invention in more detail, but are not to be construed to limit the scope thereof.

EXAMPLES

Isolation and Culture of Adipose Tissue-Derived Cell

Human adipose tissue was minced, and then digested in Hanks balance buffer salt solution (HBSS) containing 0.075% collagenase (Sigma Chemical Co.) in a 37° C. shaking water bath for 1 hour. Digests were filtered with Cell Strainer (BD Biosciences) and centrifuged at 800 g for 10 minutes. The digests were treated with an erythrocyte lysis buffer. The cells were then plated using DMEM with 10% defined fetal bovine serum (Hyclone). After 12 hours (a period during which no replication occurs (see Djian P et al., J Clin Invest. 1983: 72: 1200-1208)), the adherent adipose tissue-derived cells were washed, treated with EDTA, and re-plated at density 40,000 cells/cm$^2$ on human fibronectin-coated dishes in a culture medium I which contains 60% DMEM (low glucose), 40% MCDB201, and ITS (10.0 ng/L insulin, 5.5 mg/L transferrin and 6.7 mg of sodium selenite), 10 ng/ML EGF, 1 nM dexamethasone, 0.1 mM ascorbic acid, and 5% FCS (Hyclone). The cells were passaged 3-5 times to result adipose tissue-derived cells suitable for experiments (stage I).

Formation of Pancreatic Islet from Adipose Tissue-Derived Cell, and Differentiation Thereof to Pancreatic Endocrine Cell Adipose tissue-derived cells were treated with trypsin/EDTA (Nacalai Tesque) to dissociate. The singlenized cells were plated in culture medium II containing 80% Knock-Out™ D-MEM (basal medium optimized for growth of undifferentiated embryonic and induced pluripotent stem cells, (GIBCO Invitrogen), 20% defined fetal bovine serum, 1 mM glutamine (GIBCO Invitrogen) and 1% nonessential amino acid (GIBCO Invitrogen) in a low attachment culture dish (Hydro Cell; CellSeed Inc.). The cells were self-aggregated and formed adipospheres within hours. The resulting adipospheres (see FIG. 1) were cultured for 7 days with change of medium every 3 days (stage II).

Figure 2:
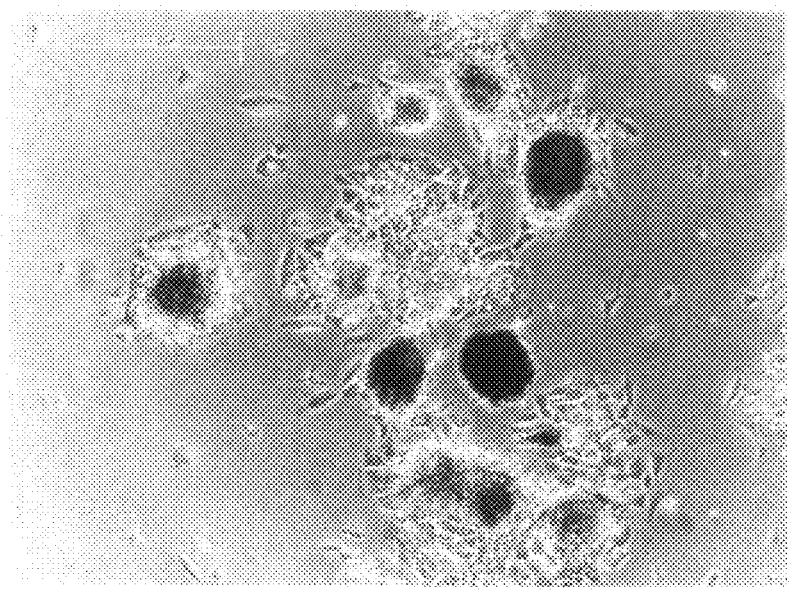
FIG. 2 is a microscope image of pancreatic precursor cells induced from adipospheres. A scale bar indicates 502 μm.

Seven-day-old adipospheres (which consisted of about 1,000 cells, on average) were plated at density of 300 cells/well in six-well plastic culture plate (Iwaki), and grown for an additional week in culture medium III which contains DMEM/F-12 (1:1) (GIBCO Invitrogen), ITS (10 mg/L insulin, 6.7 mg/L transferrin, and 5.5 mg/L selenium (all from GIBCO Invitrogen)), 1 mM glutamine and 5 μg/mL human fibronectin (Roche Diagnostics) to obtain pancreatic precursor cells (see FIG. 2) (stage III).

After one week, the pancreatic precursor cells were dissociated into single cells with trypsin/EDTA. The cells were plated on 0.1% gelatin-coated plastic tissue-culture plate (BD Bioscience) at the density of 200,000 cells/mL in culture medium IV containing DMEM/F-12 (1:1), N2 and B27 (both from GIBCO Invitrogen; added according to manufacture's instruction), 1 mM glutamine and 10 ng/ML bFGF (GIBCO Invitrogen), and cultured for 7 days to obtain pancreatic endocrine precursor cells (stage 1V). These pancreatic endocrine cells can be proliferated with passage culture.

The obtained pancreatic endocrine precursor cells were cultured in culture medium V containing DMEM (without glucose)/F-12 (1:1), N2 and B27, 1 mM glutamine, 10 mM nicotinamide (Sigma Chemical Co.), and 10 nM exendin-4 (Sigma Chemical Co.) for 7 days to obtain prepancreatic endocrine cells (stage V).

Figure 3:
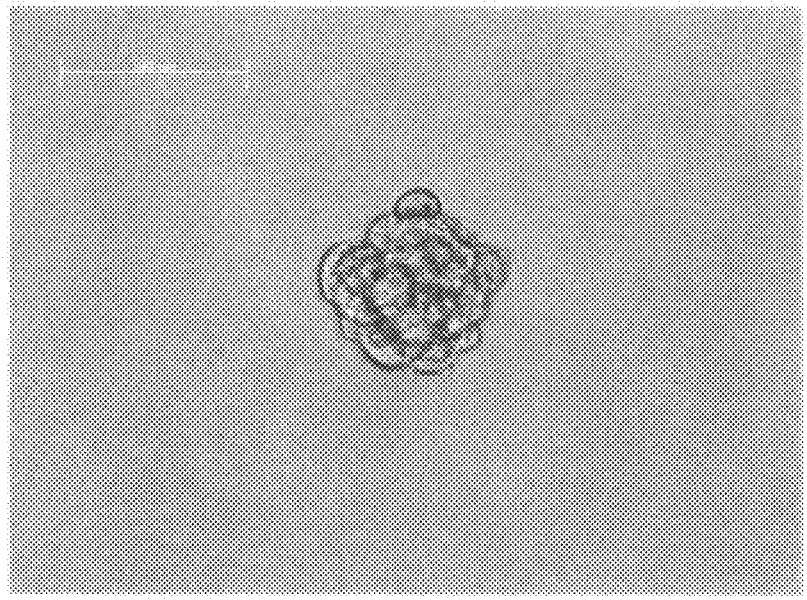
FIG. 3 is a microscope image of obtained pancreatic islets. A scale bar indicates 100 µm.

After 7 days, the obtained prepancreatic endocrine cells were dissociated and applied for a low attachment culture dish to grown in the suspension of culture medium V for 3 to 7 days to form pancreatic islets containing the pancreatic endocrine cells (see FIG. 3) (stage VI).

Reverse Transcription Polymerase Chain Reaction (RT-PCR)

Figure 4:
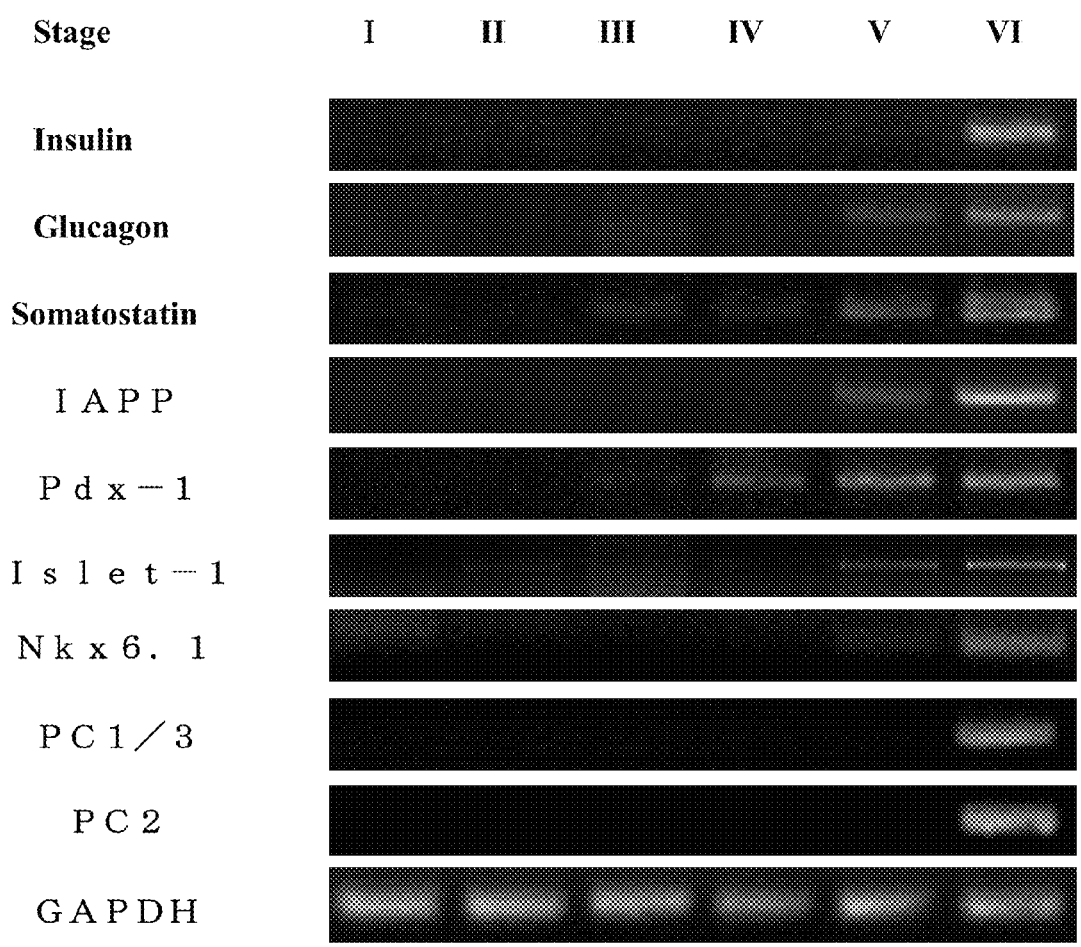
FIG. 4 is an electrophoretic image showing a result of RT-PCR using RNA from cells at stage I-VI.
Figure 5A:
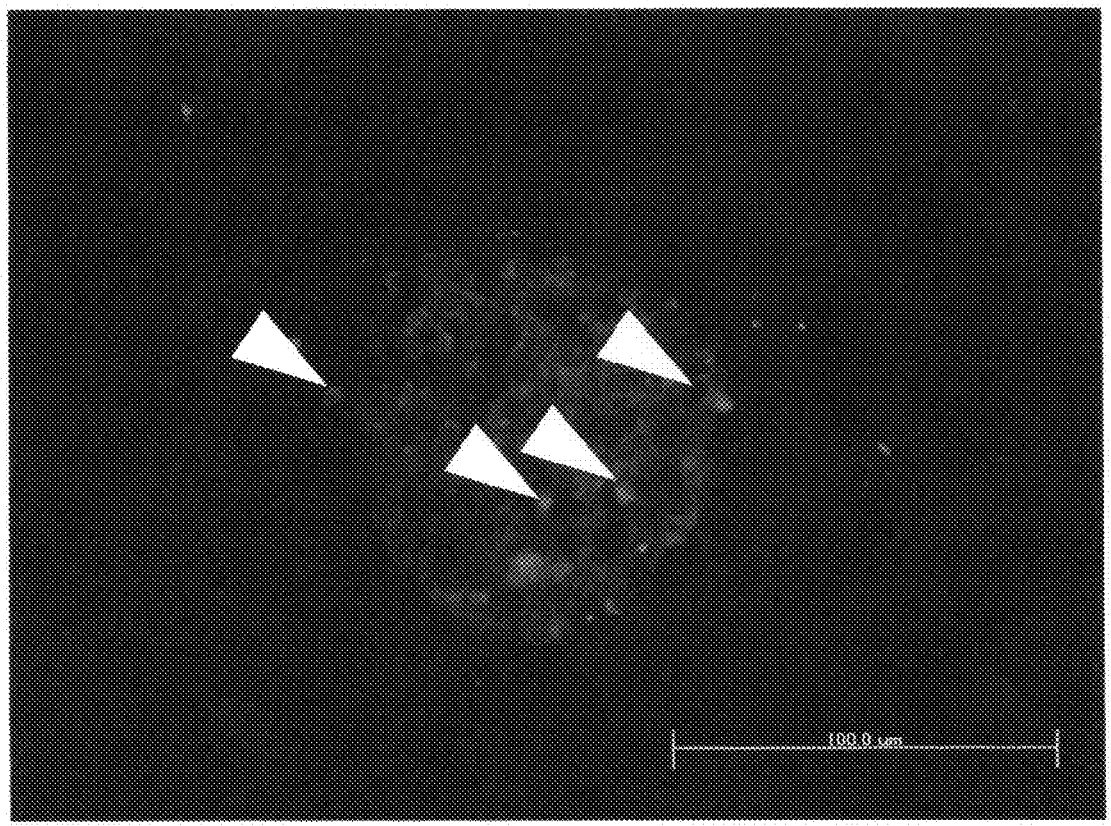
FIG. 5a is a microscope image of a C-peptide positive cell contained in a pancreatic islet with immunostaining.
Figure 5B:
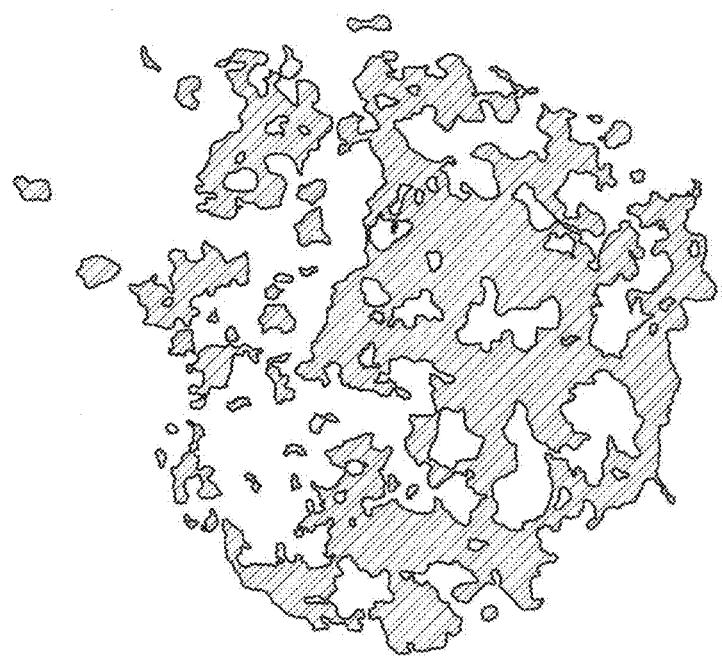
FIG. 5b is a schematic representation showing existence of a C-peptide positive cell in a pancreatic islet.
Figure 6A:
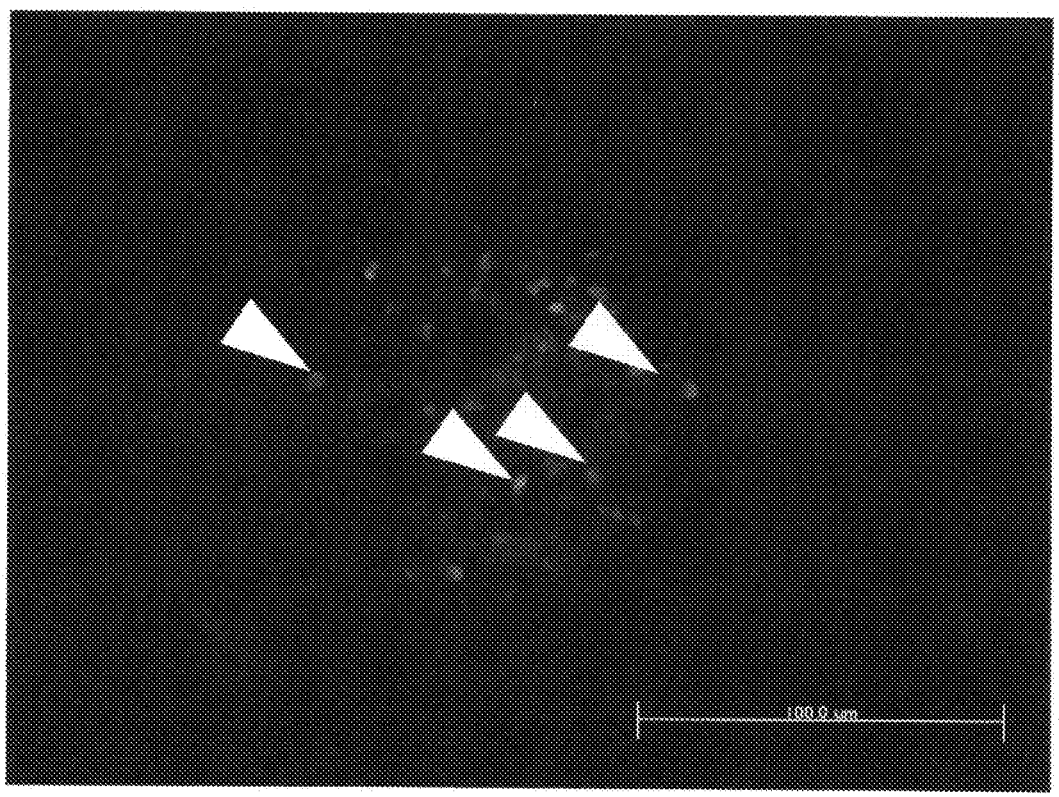
FIG. 6a is a microscope image of an insulin positive cell contained in a pancreatic islet with immunostaining.
Figure 6B:
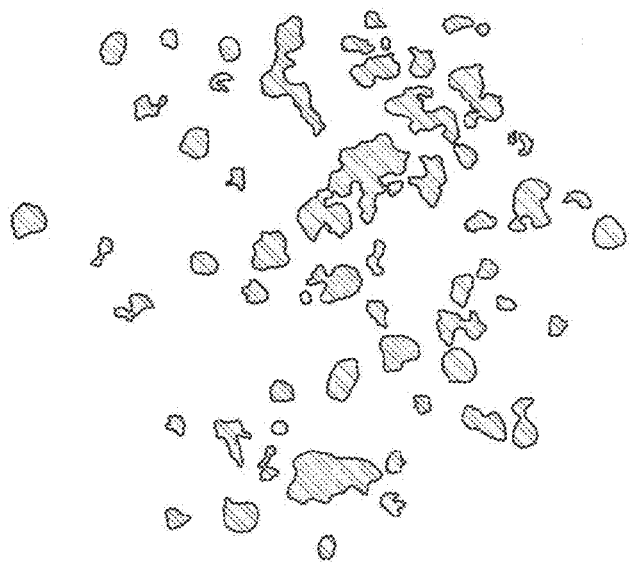
FIG. 6b is a schematic representation showing existence of an insulin positive cell in a pancreatic islet.
Figure 7A:
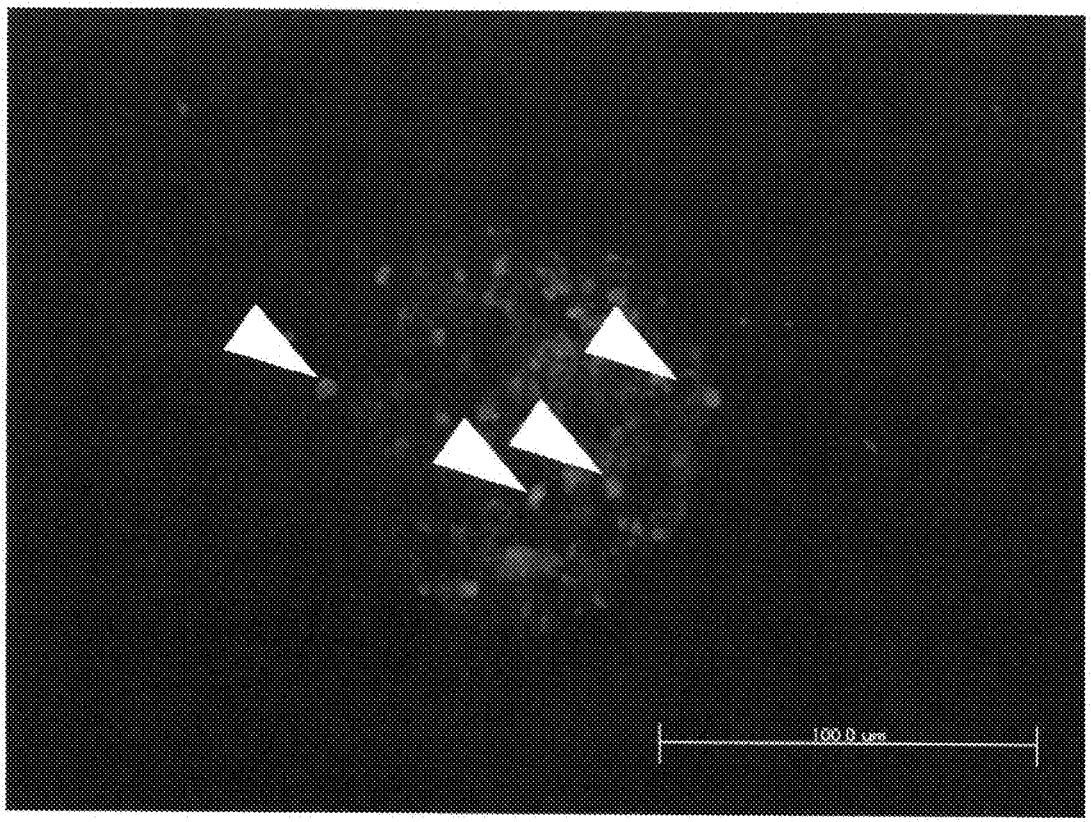
FIG. 7a is a microscope image of a C-peptide positive cell and insulin positive cell contained in a pancreatic islet with immunostaining. An arrow tip indicates a part of the cell in which C-peptide and insulin coexist.
Figure 7B:
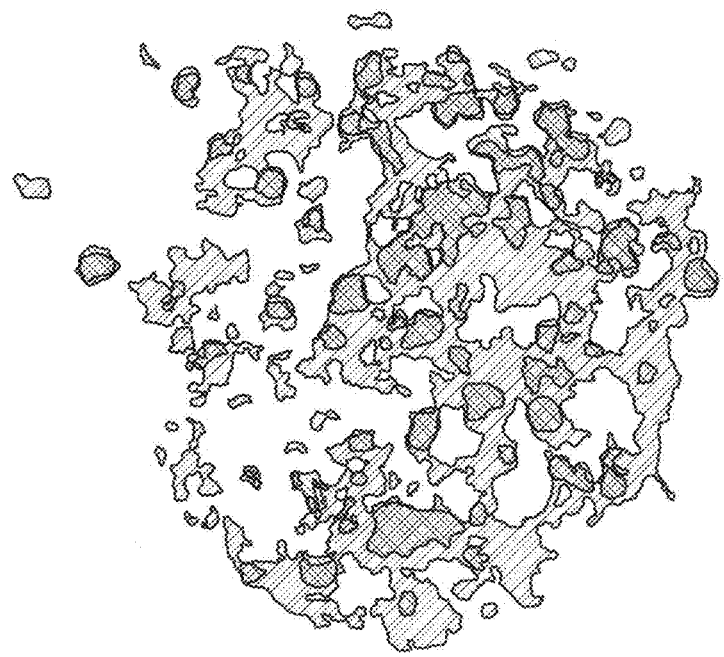
FIG. 7b is a schematic representation showing existence of a C-peptide positive cell in a pancreatic islet by a falling diagonal stroke from top right to bottom left, and existence of an insulin positive cell by a falling diagonal stroke from top left to bottom right. The portion both strokes overlap is a cell in which C-peptide and insulin coexist.
Figure 8A:
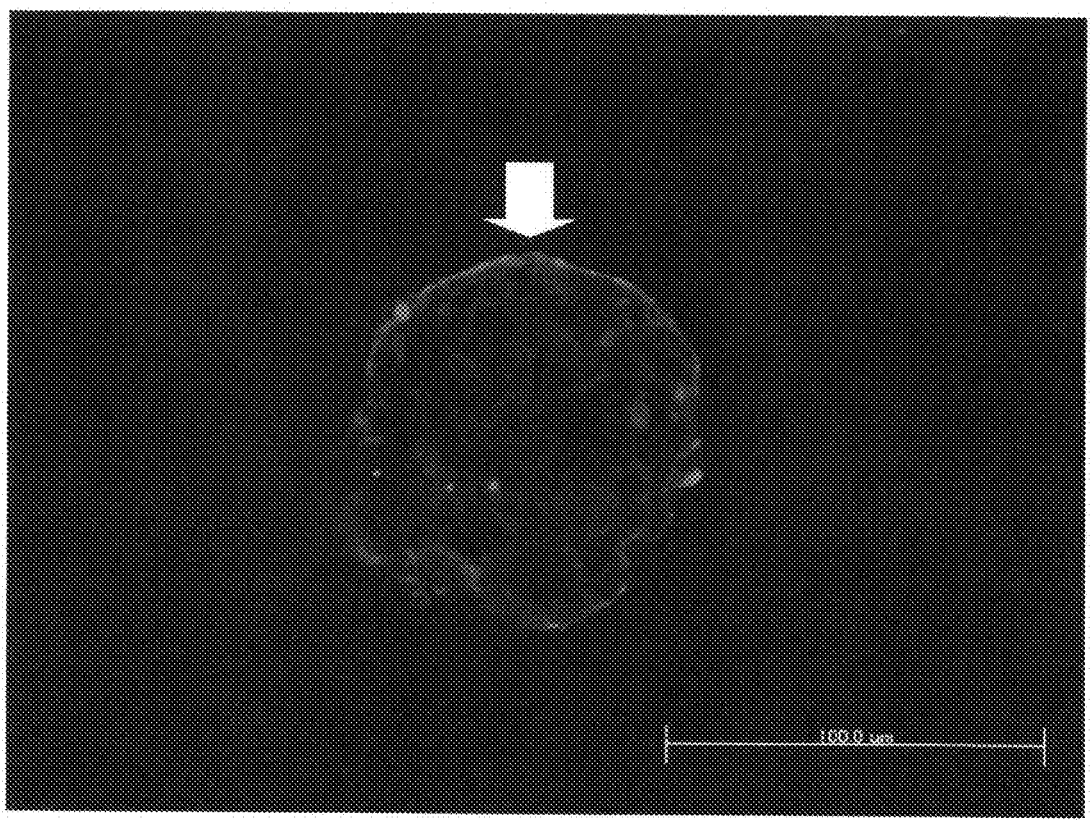
FIG. 8a is a microscope image of a glucagon positive cell contained in a pancreatic islet with immunostaining.
Figure 8B:
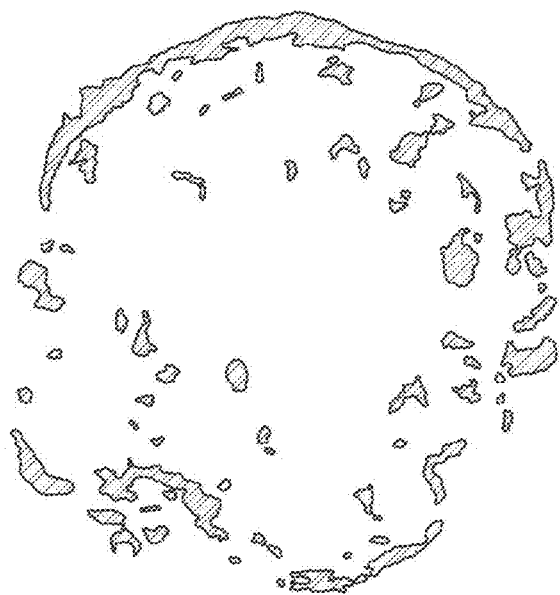
FIG. 8b is a schematic representation showing existence of a glucagon positive cell in a pancreatic islet.
Figure 9A:
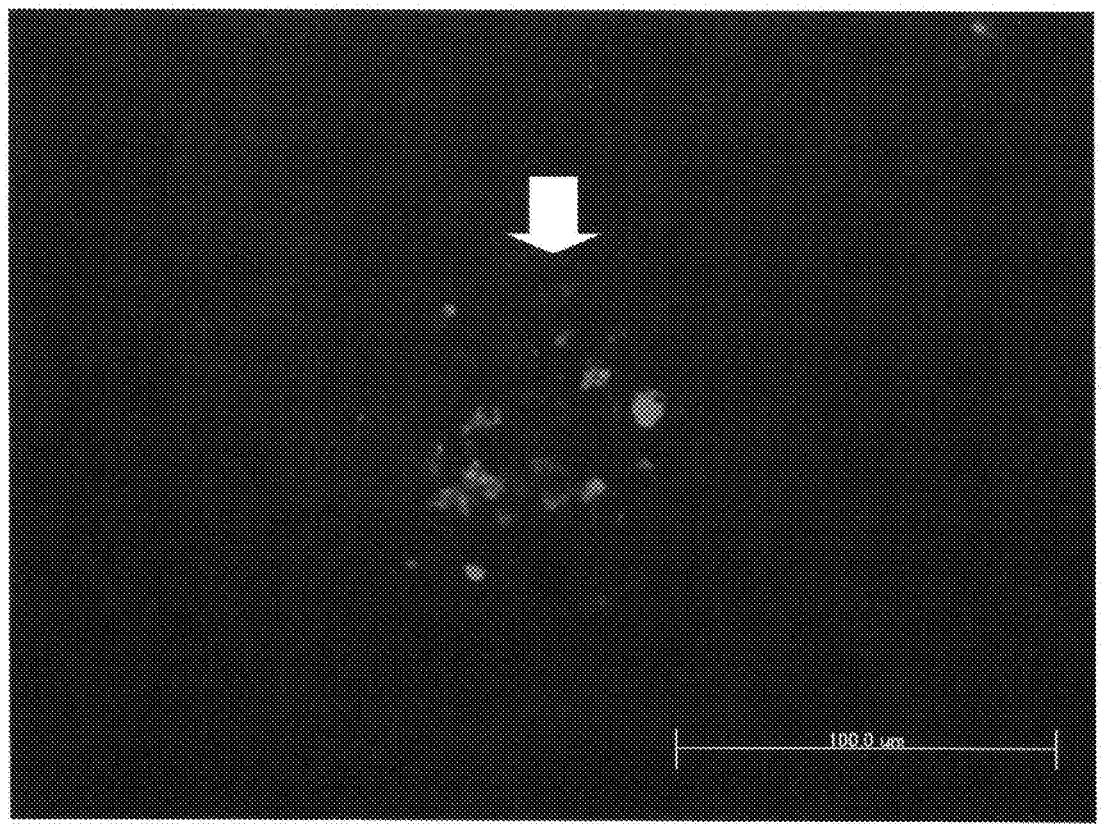
FIG. 9a is a microscope image of an insulin positive cell contained in a pancreatic islet with immunostaining.
Figure 9B:
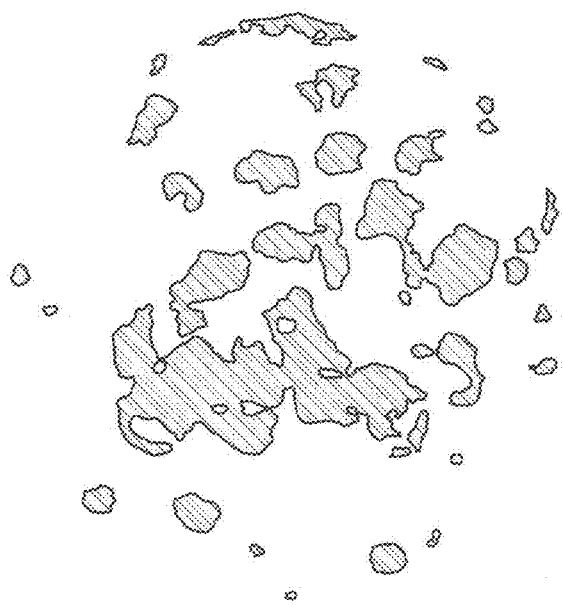
FIG. 9b is a schematic representation showing existence of an insulin positive cell in a pancreatic islet.
Figure 10A:
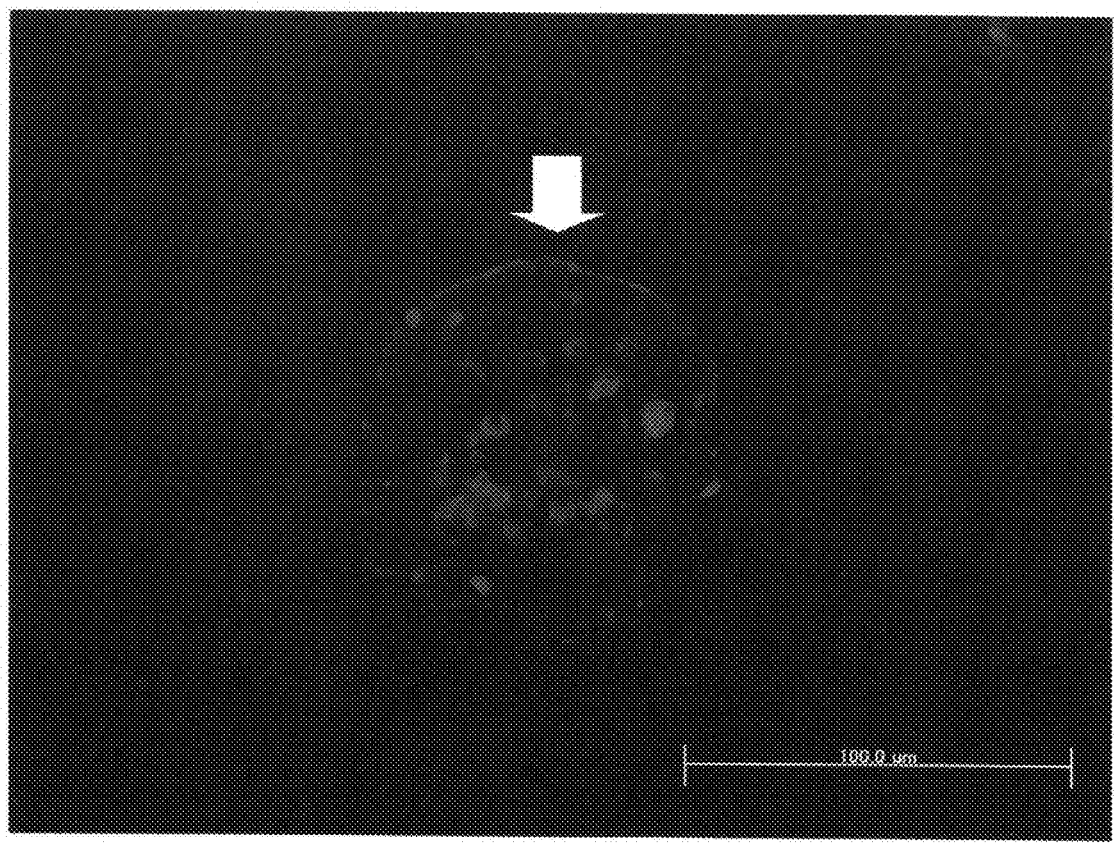
FIG. 10a is a microscope image of a glucagon positive cell and an insulin positive cell contained in a pancreatic islet with immunostaining.
Figure 10B:
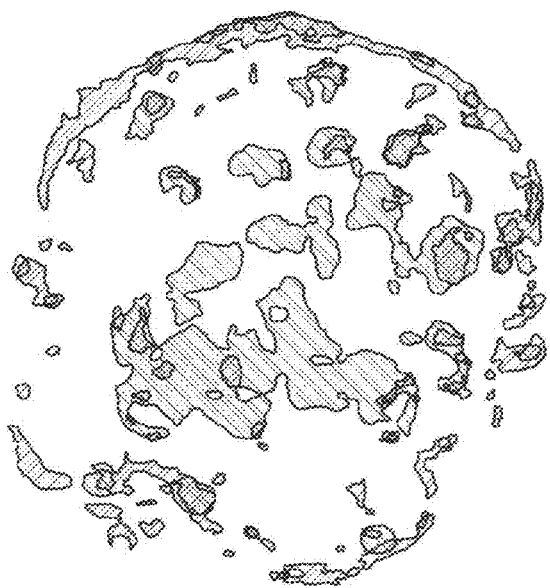
FIG. 10b is a schematic representation showing existence of a glucagon positive cell by a falling diagonal stroke from top right to bottom left, and existence of an insulin positive cell by a falling diagonal stroke from top left to bottom right in a pancreatic islet.
Figure 11A:
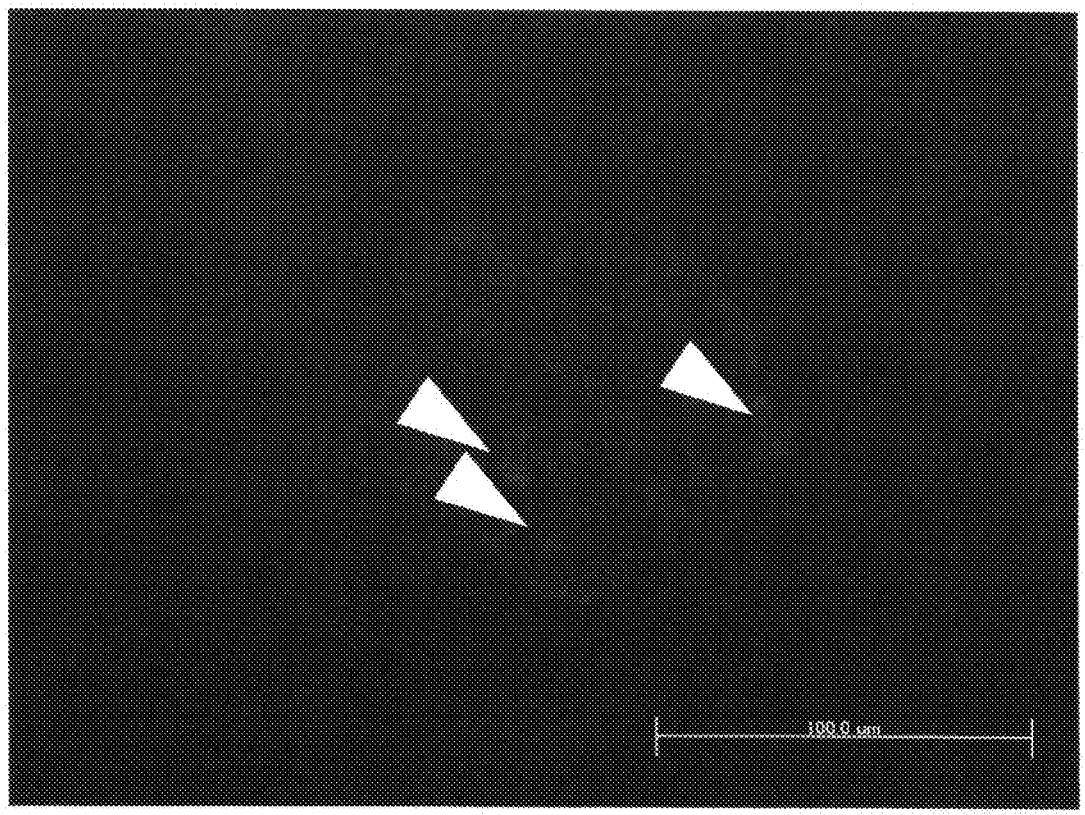
FIG. 11a is a microscope image of a somatostatin positive cell contained in a pancreatic islet with immunostaining.
Figure 11B:
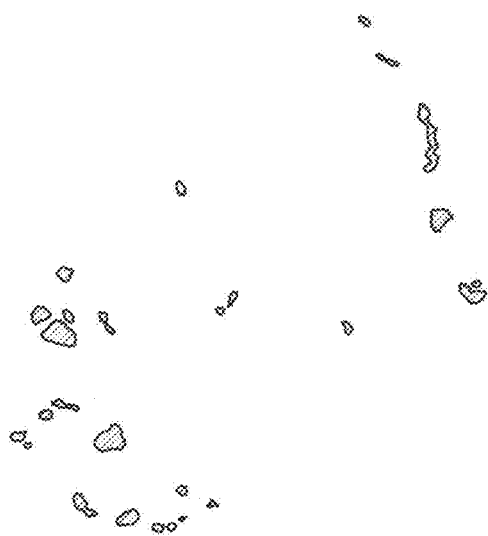
FIG. 11b is a schematic representation showing existence of a somatostatin positive cell in a pancreatic islet.
Figure 12A:
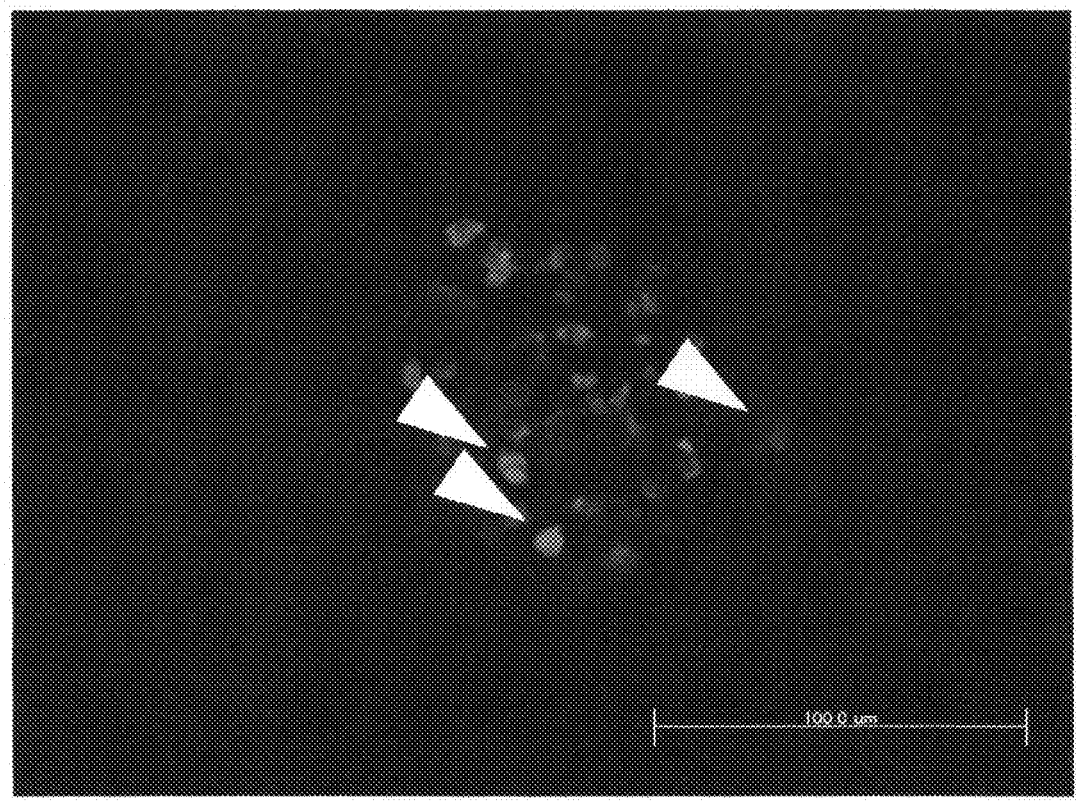
FIG. 12a is a microscope image of an insulin positive cell contained in a pancreatic islet with immunostaining.
Figure 12B:
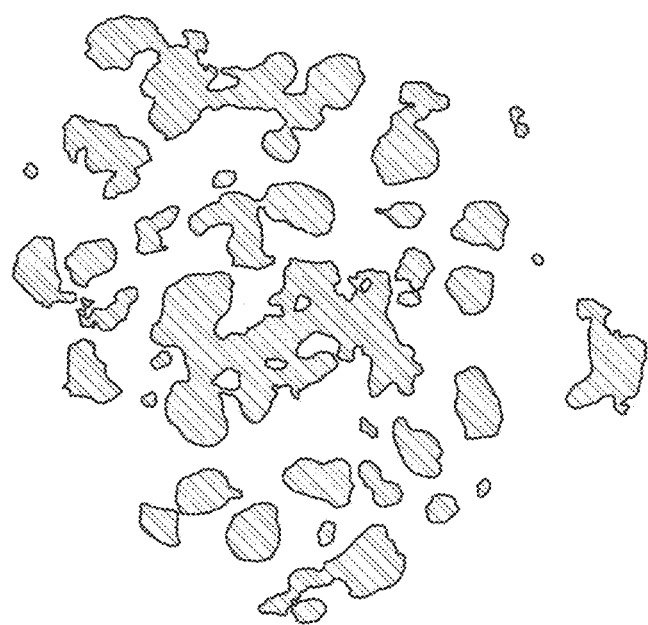
FIG. 12b is, a schematic representation showing existence of an insulin positive cell in a pancreatic islet.
Figure 13A:
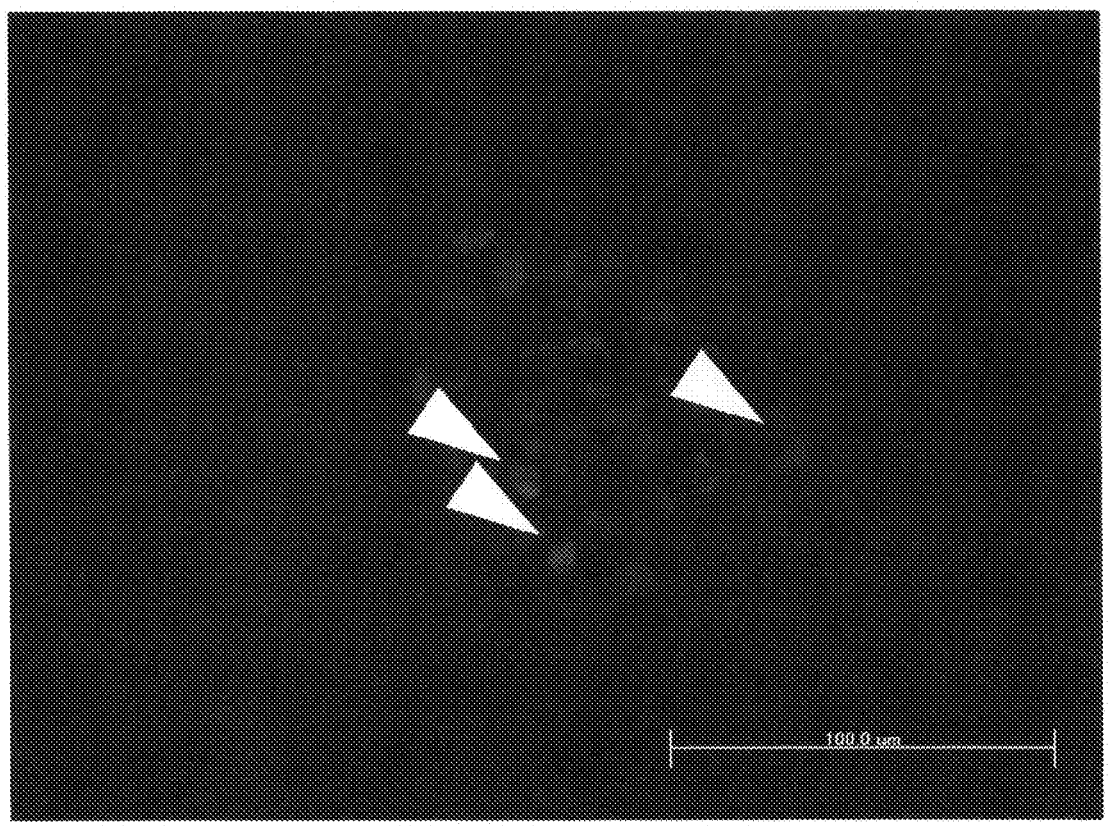
FIG. 13a is a microscope image of a somatostatin positive cell and an insulin positive cell contained in a pancreatic islet with immunostaining. An arrow tip indicates a part of the cell in which somatostatin and insulin coexist.
Figure 13B:
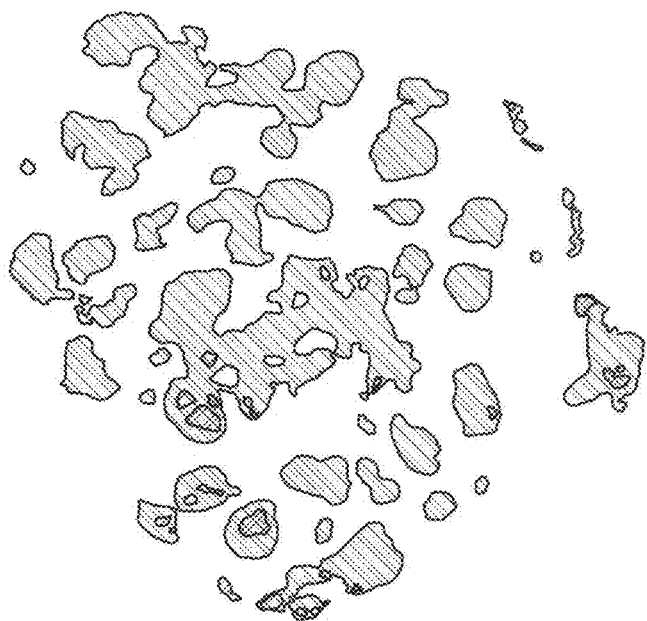
FIG. 13b is a schematic representation showing existence of a somatostatin positive cell by a falling diagonal stroke from top right to bottom left, and existence of an insulin positive cell by a falling diagonal stroke from top left to bottom right in a pancreatic islet. The portion both strokes overlap is a cell in which somatostatin and insulin coexist.

Total RNA was isolated from the cells at stage I-VI using Mag-Extractor kit (TOYOBO) according to the manufacture's recommended protocol. 500 ng of total RNA was treated with DNase, and cDNA was synthesized using Superscript III reverse transcriptase RNase H (−) (Invitrogen). For insulin, glucagon, somatostatin, IAPP, PDx-1, Islet-1, Nkx6.1, PC1/3, PC2, and GAPDH, RT-PCR was performed using KOD-plus (TOYOBO) as follows: denaturation at 94° C. for 2 minutes, followed by 40 cycles of denaturation at 94° C. for 15 seconds, annealing at predetermined temperature for 30 seconds and elongation at 68° C. for 30 seconds. The annealing temperature and the primer sequence are shown in Table 1. The resulting amplification products were electrophoresed in 2% agarose gel. The results are shown in FIG. 4. It was confirmed that the cells at Stage VI express insulin, expression of hormones from pancreatic islets, glucagon and somatostatin, and transcription factors, IAPP PDX-1, ISLET-1 and NKX6.1 is increased with differentiation, and the cells at Stage VI express converting enzymes of insulin protein, PC1/3 and PC2. It was found that pancreatic islets and pancreatic endocrine cells can be obtained from adipose tissue-derived cells.

TABLE 1

| Gene | Primer sequence | SEQ ID NO | Size of amplification product (bP) | Annealing temperature (° C.) |
| --- | --- | --- | --- | --- |
| Insulin | AGCCTTTGTGAACCAACACC<br>GCTGGTAGAGGGAGCAGATG | SEQ ID NO: 1<br>SEQ ID NO: 2 | 245 | 60 |
| Glucagon | AGGCAGACCCACTCAGTGA<br>AACAATGGCGACCTCTTCTG | SEQ ID NO: 3<br>SEQ ID NO: 4 | 308 | 55 |
| Somatostatin | TGCGCTGTCCATCGTCCT<br>GCCATAGCCGGGTTTGAGTT | SEQ ID NO: 5<br>SEQ ID NO: 6 | 257 | 55 |
| IAPP | GAGAGAGCCACTGAATTACTTGCC<br>CCTGACCTTATCGTGATCTGCC | SEQ ID NO: 7<br>SEQ ID NO: 8 | 471 | 60 |

TABLE 1-continued

| Gene | Primer sequence | SEQ ID NO | Size of amplification product (bP) | Annealing temperature (° C.) |
|---|---|---|---|---|
| Pdx-1 | GGATGAAGTCTACCAAAGCTCACGC<br>CCAGATCTTGATGTGTCTCTCGGTC | SEQ ID NO: 9<br>SEQ ID NO: 10 | 230 | 60 |
| Islet-1 | GATTTCCCTATGTGTTGGTTGC<br>CTTCCACTGGGTTAGCCTGTAA | SEQ ID NO: 11<br>SEQ ID NO: 12 | 827 | 60 |
| Nkx6.1 | GTTCCTCCTCCTCCTCTTCCTC<br>AAGATCTGCTGTCCGGRAAAAG | SEQ ID NO: 13<br>SEQ ID NO: 14 | 381 | 55 |
| PC1/3 | TTGGCTGAAAGAGAACGGGATACATCT<br>ACTTCTTTGGTGATTGCTTTGGCGGTG | SEQ ID NO: 15<br>SEQ ID NO: 16 | 457 | 60 |
| PC2 | GCATCAAGCACAGACCTACACTCG<br>GAGACACAACCACCCTTCATCCTTC | SEQ ID NO: 17<br>SEQ ID NO: 18 | 309 | 60 |
| GAPDH | GTCAGTGGTGGACCTGACCT<br>AGGGGAGATTCAGTGTGGTG | SEQ ID NO: 19<br>SEQ ID NO: 20 | 394 | 60 |

Confirming Localization of Insulin, C-Peptide, Glucagon, and Somatostatin in Pancreatic Islet with Immunostaining The pancreatic islets obtained by the method described above were fixed with 4% paraformaldehyde for 24 hours. After washing with PBS, it was embedded in OTC compound and frozen. Then it was sliced into 7 μm of thin sections, and they were placed on slide glasses to be air-dried. The obtained slide glasses were washed with PBS, and blocked on Block One (Nacarai Tesque) for 60 minutes. After washing with PBS, they were reacted with a guinea pig anti insulin antibody, a Texas red-labeled anti guinea pig IgG antibody, and a rabbit anti C-peptide antibody, and finally with a FITC-labeled anti rabbit IgG antibody. Likewise, after reacting with a guinea pig anti insulin antibody, a Texas red-labeled anti guinea pig IgG antibody, they were reacted with a rabbit anti glucagon antibody, followed by a FITC-labeled anti rabbit IgG antibody, or with an rabbit anti somatostatin antibody, followed by a FITC-labeled anti rabbit antibody. After washing, they were observed under fluorescence microscope. The results are shown in FIGS. 5 to 13. It was confirmed that insulin positive cells exist mainly in the inside of the pancreatic islets, and they are similar to those in pancreatic islets in a living body. Moreover, it was found that insulin and C-peptide coexist in the pancreatic islet. Thereby, it was revealed that the insulin is biosynthesized within cells. It was confirmed that glucagon positive cells exist outside of the pancreatic islets like covering the islets, and they are similar to those in pancreatic islets in a living body. Furthermore, it was confirmed that there are both of the cell in which insulin and somatostatin coexist, and the cell in which insulin and somatostatin do not coexist (the cell in which insulin and somatostatin coexist are indicated by arrow tips in FIGS. 11s, 12s and 13a). This is because insulin secreting cells transiently express both insulin and somatostatin in the process of differentiation.

Quantifying Secreted amount of Insulin and C-Peptide with ELISA

Figure 14:
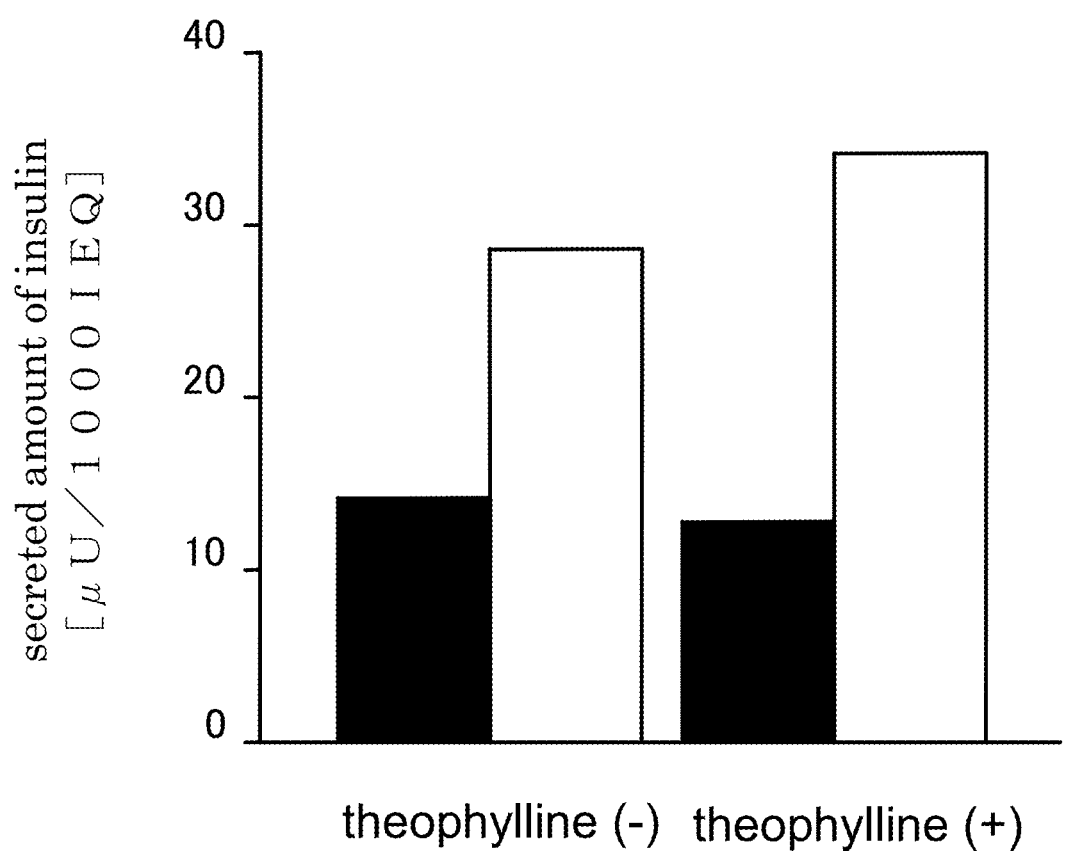
FIG. 14 is a graph showing the amount of insulin secreted from the obtained pancreatic islet. Black represents the amount in the presence of 3.3 mM glucose, and white represents the amount in the presence of 16.7 mM glucose.
Figure 15:
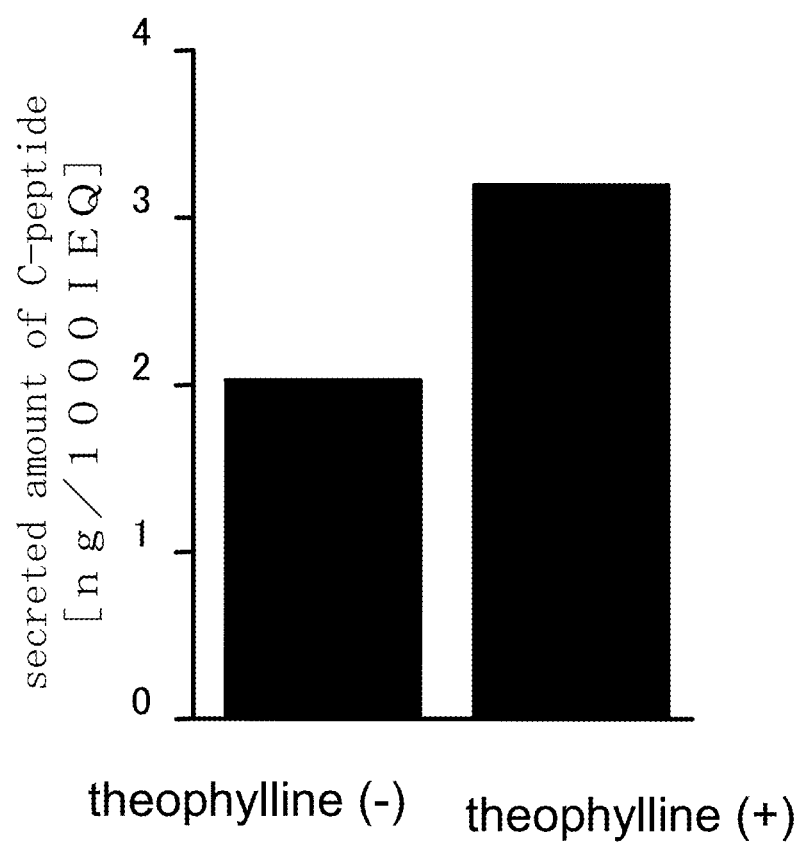
FIG. 15 is a graph showing the amount of secreted C-peptide in the presence of 16.7 mM glucose.
Figure 16:
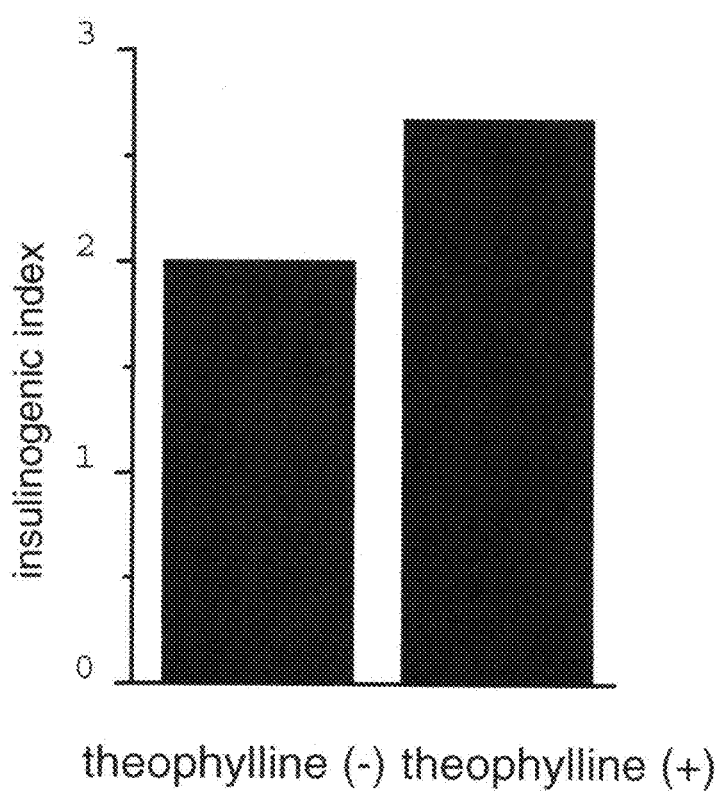
FIG. 16 is a graph showing the insulinogenic index in the presence of 3.3 mM glucose.

The pancreatic islets obtained by the method as described above were washed three times with RPMI 1640 (11879-020; GIBCO Invitrogen), and preincubated for 1 hour with RPMI 1640 containing 0.5% bovine serum albumin and 3.3 mM glucose. The pancreatic islets were then incubated in RPMI 1640 containing 3.3 mM or 16.7 mM glucose for 2 hours. As a control, RPMI 1640 containing 10 mM theophylline was used. The insulin level and the C-peptide level in the culture supernatant were measured using ELISA kit (Mercodia). The results are shown in FIGS. 14, 15 and 16. The pancreatic islets which were cultured in the culture medium without theophylline known as a substance which promotes secretion of insulin secreted the amount similar to those secreted by the pancreatic islets which were cultured in the culture medium containing theophylline. Therefore, it was confirmed that the pancreatic islets obtained from adipose tissue-derived cells have sufficient insulinogenic index.

Figure 17:
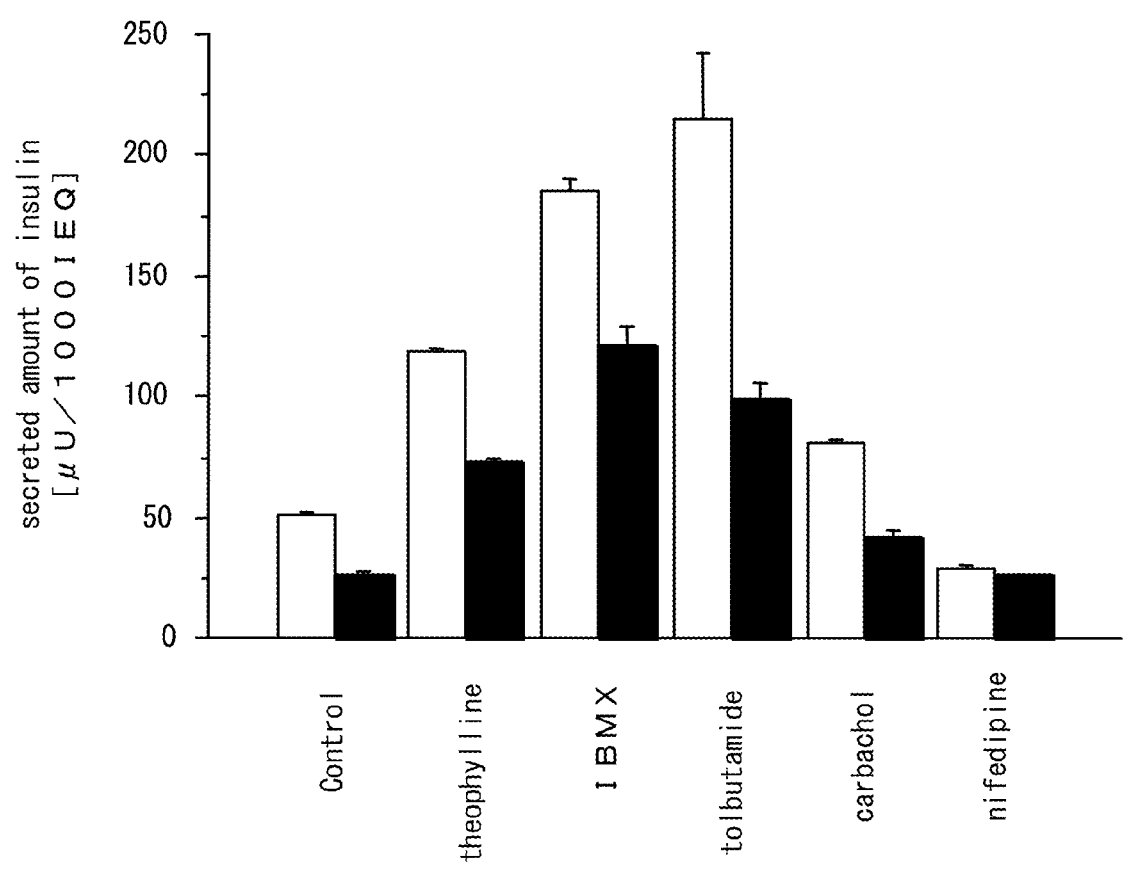
FIG. 17 is a graph showing that an insulin secretagogue promotes insulin secretion from a pancreatic islet. Black represents the amount in the presence of 3.3 mM glucose, and white represents the amount in the presence of 16.7 mM glucose.

As described above, the pancreatic islets were incubated in RPMI 1640 containing 3.3 mM or 16.7 mM glucose, 100 μM theophylline, 100 μM IBMX, 10 μM tolbutamide, 100 μM carbachol or 50 μM nifedipine for 2 hours, and the secreted amounts of insulin were measured. The results are shown in FIG. 17. It was confirmed that secretion of insulin is promoted by theophylline, IBMX, tolbutamide, and carbachol that are known to promote the secretion of insulin. It was confirmed that the secretion of insulin response to glucose is suppressed by nifedipine that is known to suppress the secretion of insulin.

Transplantation of Insulin Secreting Cell

Figure 18:
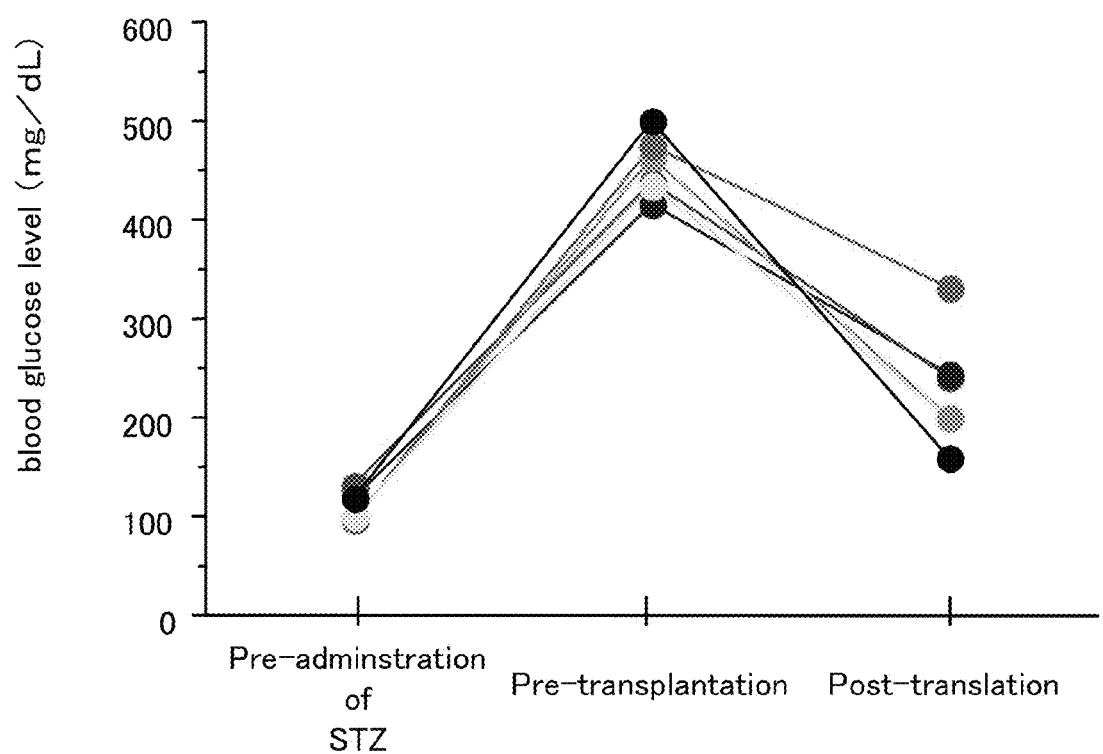
FIG. 18 is a graph showing that the blood glucose level is decreased by transplanting a pancreatic islet.

To NOD/SCID mice (eight-week-old, male, six individuals), 50 mg/kg streptozotocin (STZ) was administered once a day from Day-11 to day −7 to destroy their pancreas Langerhans islets. On day 0, 500 of insulin-secreting cell masses were transplanted under left renal capsule. The levels of blood glucose were measured on Day −11, Day 0, and Day 14. The results are shown in FIG. 18. It was confirmed that by transplanting insulin-secreting cell masses, the level of blood glucose is decreased.

INDUSTRIAL APPLICABILITY

The present invention provides a method for obtaining pancreatic endocrine cells from adipose tissue-derived cells, pancreatic endocrine cells obtainable by the method, a method for screening a substance which promotes or suppresses differentiation to pancreatic endocrine cells, a kit therefore and the like. Therefore, the present invention can be used in the fields of medicine and the like, for example, the field of the development or preparation of the medicine for the prevention, treatment or diagnosis of diabetes and various diseased induced by it.

[Sequence Table Free Text]
SEQ ID NO: 1: PCR forward primer to amplify insulin mRNA
SEQ ID NO: 2: PCR reverse primer to amplify insulin mRNA
SEQ ID NO: 3: PCR forward primer to amplify Glucagon mRNA
SEQ ID NO: 4: PCR reverse primer to amplify Glucagon mRNA
SEQ ID NO: 5: PCR forward primer to amplify Somtatostatin mRNA
SEQ ID NO: 6: PCR reverse primer to amplify Somatostatin mRNA
SEQ ID NO: 7: PCR forward primer to amplify IAPP mRNA
SEQ ID NO: 8: PCR reverse primer to amplify IAPP mRNA
SEQ ID NO: 9: PCR forward primer to amplify Pdx-1 mRNA
SEQ ID NO: 10: PCR reverse primer to amplify Pdx-1 mRNA
SEQ ID NO: 11: PCR forward primer to amplify Islet-1 mRNA
SEQ ID NO: 12: PCR reverse primer to amplify Islet-1 mRNA
SEQ ID NO: 13: PCR forward primer to amplify Nkx6.1 mRNA
SEQ ID NO: 14: PCR reverse primer to amplify Nkx6.1 mRNA
SEQ ID NO: 15: PCR forward primer to amplify PC1/3 mRNA
SEQ ID NO: 16: PCR reverse primer to amplify PC1/3 mRNA
SEQ ID NO: 17: PCR forward primer to amplify PC2 mRNA
SEQ ID NO: 18: PCR reverse primer to amplify PC2 mRNA
SEQ ID NO: 19: PCR forward primer to amplify GAPDH mRNA
SEQ ID NO: 20: PCR reverse primer to amplify GAPDH mRNA

[Sequence Table]

What is claimed is:

1. A method for preparing undifferentiated cells from adipose tissues comprising:
   (a) digesting the adipose tissues,
   (b) removing erythrocytes from the digested adipose tissues to obtain adipose tissue-derived cells,
   (c) plating the adipose tissue-derived cells into a culture container for 12 hours,
   (d) treating the plated adipose tissue-derived cells with EDTA that does not contain trypsin to obtain undifferentiated cells, and culturing the undifferentiated cells in a suspended state, and
   (e) isolating the undifferentiated cells in the step (d).

* * * * *